(12) United States Patent
Wilson et al.

(10) Patent No.: US 8,080,375 B2
(45) Date of Patent: Dec. 20, 2011

(54) METHODS AND KITS FOR DETECTING AN ENZYME CAPABLE OF MODIFYING A NUCLEIC ACID

(75) Inventors: Stuart Wilson, London (GB); John Christopher Stanley, Cambridgeshire (GB); Sharon Banin, London (GB)

(73) Assignee: Iseao Technologies Limited, London (GB)

( * ) Notice: Subject to any disclaimer, the term of this patent is extended or adjusted under 35 U.S.C. 154(b) by 549 days.

(21) Appl. No.: 11/914,697

(22) PCT Filed: May 18, 2006

(86) PCT No.: PCT/GB2006/001831
§ 371 (c)(1),
(2), (4) Date: Mar. 26, 2008

(87) PCT Pub. No.: WO2006/123154
PCT Pub. Date: Nov. 23, 2006

(65) Prior Publication Data
US 2009/0098539 A1    Apr. 16, 2009

(30) Foreign Application Priority Data

May 18, 2005  (GB) .................................. 0510133.2
Apr. 20, 2006  (GB) .................................. 0607862.0

(51) Int. Cl.
*C12Q 1/68*       (2006.01)
(52) U.S. Cl. ...................................................... 435/6.1
(58) Field of Classification Search ........................ None
See application file for complete search history.

(56) References Cited

U.S. PATENT DOCUMENTS

| 5,049,490 | A  | * | 9/1991  | Sutherland et al. ............. 435/6 |
| 5,436,143 | A  | * | 7/1995  | Hyman ....................... 435/91.2 |
| 5,516,663 | A  | * | 5/1996  | Backman et al. ............. 435/91.2 |
| 6,100,028 | A  | * | 8/2000  | Cole et al. ...................... 435/6 |
| 6,238,864 | B1 | * | 5/2001  | Yan .................................. 435/6 |
| 6,548,268 | B1 | * | 4/2003  | Rambach ........................ 435/34 |
| 6,642,000 | B1 | * | 11/2003 | Strizhkov et al. ................. 435/6 |
| 6,753,177 | B1 |   | 6/2004  | Stocker et al. |
| 2005/0118665 | A1 | * | 6/2005 | Zhou et al. ...................... 435/23 |

FOREIGN PATENT DOCUMENTS

EP     0 599 270       6/1994
WO   WO 2005/012567   2/2005

OTHER PUBLICATIONS

Anonymous: Internet Article; XP002398001; URL:http://www.bdbiosciences.com/nvCategory.jsp?action=SELECT&form=formTree_catBean&item=112351>.
Banin, S. et al.: "Demonstration of an Alternative Approach to Immuno-PCR" Clinical Chemistry, American Association for Clinical Chemistry, vol. 50, No. 10, Oct. 2004, pp. 1932-1934, XP001203947.
Niemeyer C M et al. "Immuno-PCR: high sensitivity detection of proteins by nucleic acid amplification", Trends in Biotechnology, vol. 23, No. 4, Apr. 2005.
Banin, S. et al. "Indirect immuno-PCR (i2PCR). Development of a simplified 'one step' protocol." Poster presented at AACC Oak Ridge Conference, San Jose, CA, Apr. 2006.
Office Action issued on Jun. 4, 2010 for EP Application No. 06727136.1.
Claims currently pending in EP Application No. 06727136.1 upon which the Office Action dated Jun. 4, 2010 was based.

* cited by examiner

*Primary Examiner* — Christopher M. Babic
(74) *Attorney, Agent, or Firm* — Lucas & Mercanti, LLP

(57)         ABSTRACT

An improved method of detecting an enzyme in a sample, which enzyme is capable of adding or removing a chemical moiety to or from a nucleic acid molecule, thereby conferring the nucleic acid molecule with the ability to be extended to generate a novel detectable nucleic acid molecule, comprises the steps of allowing the sample to be tested for the presence of the enzyme to interact with the nucleic acid molecule; and testing for interaction of the enzyme with the nucleic acid molecule by detecting the novel nucleic acid molecule generated only in the presence of the enzyme. The preferred enzyme is a phosphatase. The methods have a number of applications, for example in enhancing the sensitivity of immunoassays, for detecting pathogen associated phosphatase, for diagnosing certain conditions and for detecting specific contaminants in a sample.

15 Claims, 9 Drawing Sheets

Conditions A     Conditions B

Dilutions S-AP   $10^{-5}$   $10^{-6}$   $10^{-7}$   0   $10^{-5}$   $10^{-6}$   $10^{-7}$   0

25 cycles of PCR 30 cycles of PCR

AMPAQ results   0.07   0.02   0.02   0.02   0.06   0.03   0.02   0.02
(OD values)

Dilutions S-AP     $10^{-4}$   $10^{-5}$   $10^{-6}$   $10^{-7}$   $10^{-8}$   $10^{-9}$   0

30 cycles of PCR

AMPAQ results   1.43   0.68   0.07   0.02   0.03   0.01   0.02
(OD values)

Dilutions S-AP     $10^{-7}$   $10^{-9}$   $10^{-11}$   0

25 cycles of PCR

SEQUENCE LISTING

```
<160> NUMBER OF SEQ ID NOS: 27

<210> SEQ ID NO 1
<211> LENGTH: 45
<212> TYPE: DNA
<213> ORGANISM: Artificial sequence
<220> FEATURE:
<223> OTHER INFORMATION: Oligonucleotide
<220> FEATURE:
<221> NAME/KEY: Biotin
<222> LOCATION: (1)..(1)
<223> OTHER INFORMATION: Biotin molecule attached to 5' end

<400> SEQUENCE: 1
gccgatatcg gacaacgccg aactgcgaag ggcgaattcc tcgtc          45

<210> SEQ ID NO 2
<211> LENGTH: 45
<212> TYPE: DNA
<213> ORGANISM: Artificial sequence
<220> FEATURE:
<223> OTHER INFORMATION: Oligonucleotide#

<400> SEQUENCE: 2
gacgaggaat tcgcccttcg cagttcggcg ttgtccgata tcggc          45

<210> SEQ ID NO 3
<211> LENGTH: 19
<212> TYPE: DNA
<213> ORGANISM: Artificial sequence
<220> FEATURE:
<223> OTHER INFORMATION: oligonucleotide

<400> SEQUENCE: 3
aattacgacc acatcaacc                                       19

<210> SEQ ID NO 4
<211> LENGTH: 17
<212> TYPE: DNA
<213> ORGANISM: Artificial sequence
<220> FEATURE:
<223> OTHER INFORMATION: Oligonucleotide

<400> SEQUENCE: 4
ccggttgatg tggtcgt                                         17

<210> SEQ ID NO 5
<211> LENGTH: 40
<212> TYPE: DNA
<213> ORGANISM: Artificial sequence
<220> FEATURE:
<223> OTHER INFORMATION: Oligonucleotide

<400> SEQUENCE: 5
```
aattggtcat cagccgcgtg gcctttgtca ccgacgccta                          40

<210> SEQ ID NO 6
<211> LENGTH: 38
<212> TYPE: DNA
<213> ORGANISM: Artificial sequence
<220> FEATURE:
<223> OTHER INFORMATION: Oligonucleotide
<220> FEATURE:
<221> NAME/KEY: Phosphate
<222> LOCATION: (1)..(1)
<223> OTHER INFORMATION: 5' end labelled with phosphate group

<400> SEQUENCE: 6
cctaggcgtc ggtgacaaag gccacgcggc tgatgacc                            38

<210> SEQ ID NO 7
<211> LENGTH: 24
<212> TYPE: DNA
<213> ORGANISM: Artificial sequence
<220> FEATURE:
<223> OTHER INFORMATION: Primer

<400> SEQUENCE: 7
ggacaacgcc gaactgcgaa gggc                                           24

<210> SEQ ID NO 8
<211> LENGTH: 24
<212> TYPE: DNA
<213> ORGANISM: Artificial sequence
<220> FEATURE:
<223> OTHER INFORMATION: Reverse primer

<400> SEQUENCE: 8
taggcgtcgg tgacaaaggc cacg                                           24

<210> SEQ ID NO 9
<211> LENGTH: 44
<212> TYPE: DNA
<213> ORGANISM: Artificial sequence
<220> FEATURE:
<223> OTHER INFORMATION: oligonucleotide
<220> FEATURE:
<221> NAME/KEY: Biotin
<222> LOCATION: (1)..(1)
<223> OTHER INFORMATION: 5' end labelled with biotin

<400> SEQUENCE: 9
gccgatatcg gacaacgccg aactgcgaag ggcgaaggct cgtc                     44

<210> SEQ ID NO 10
<211> LENGTH: 44
<212> TYPE: DNA
<213> ORGANISM: Artificial sequence
<220> FEATURE:
<223> OTHER INFORMATION: Oligonucleotide

<400> SEQUENCE: 10
gacgagcctt ggcccttcgc agttcggcgt tgtccgatat cggc                     44

<210> SEQ ID NO 11
<211> LENGTH: 19
<212> TYPE: DNA
<213> ORGANISM: Artificial sequence
<220> FEATURE:
<223> OTHER INFORMATION: Oligonucleotide

<400> SEQUENCE: 11

```
caagacgacc acatcaacc                                                    19
```

```
<210> SEQ ID NO 12
<211> LENGTH: 17
<212> TYPE: DNA
<213> ORGANISM: Artificial sequence
<220> FEATURE:
<223> OTHER INFORMATION: Oligonucleotide

<400> SEQUENCE: 12
ccggttgatg tggtcgt                                                      17
```

```
<210> SEQ ID NO 13
<211> LENGTH: 40
<212> TYPE: DNA
<213> ORGANISM: Artificial sequence
<220> FEATURE:
<223> OTHER INFORMATION: Oligonucleotide

<400> SEQUENCE: 13
caagcgtcat cagccgcgtg gcctttgtca ccgacgccta                             40
```

```
<210> SEQ ID NO 14
<211> LENGTH: 38
<212> TYPE: DNA
<213> ORGANISM: Artificial sequence
<220> FEATURE:
<223> OTHER INFORMATION: Oligonucleotide

<400> SEQUENCE: 14
cctaggcgtc ggtgacaaag gccacgcggc tgatgacg                               38
```

```
<210> SEQ ID NO 15
<211> LENGTH: 42
<212> TYPE: DNA
<213> ORGANISM: Artificial sequence
<220> FEATURE:
<223> OTHER INFORMATION: Oligonucleotide
<220> FEATURE:
<221> NAME/KEY: Phosphate
<222> LOCATION: (42)..(42)
<223> OTHER INFORMATION: 3' end labelled with phosphate group

<400> SEQUENCE: 15
gccgatatcg gacaacgccg aactgcgaag ggccaaggct cg                          42
```

```
<210> SEQ ID NO 16
<211> LENGTH: 38
<212> TYPE: DNA
<213> ORGANISM: Artificial sequence
<220> FEATURE:
<223> OTHER INFORMATION: Oligonucleotide
<220> FEATURE:
<221> NAME/KEY: Biotin
<222> LOCATION: (38)..(38)
<223> OTHER INFORMATION: Biotin attached to 3' end

<400> SEQUENCE: 16
ccttggccct tcgcagttcg gcgttgtccg atatcggc                               38
```

```
<210> SEQ ID NO 17
<211> LENGTH: 36
<212> TYPE: DNA
<213> ORGANISM: Artificial sequence
<220> FEATURE:
<223> OTHER INFORMATION: Oligonucleotide

<400> SEQUENCE: 17
```
ggtcatcagc cgcgtggcct ttgtcaccga cgccta                                    36

<210> SEQ ID NO 18
<211> LENGTH: 36
<212> TYPE: DNA
<213> ORGANISM: Artificial sequence
<220> FEATURE:
<223> OTHER INFORMATION: Oligonucleotide
<220> FEATURE:
<221> NAME/KEY: Phosphate
<222> LOCATION: (1)..(1)
<223> OTHER INFORMATION: 5' phosphate group

<400> SEQUENCE: 18
taggcgtcgg tgacaaaggc cacgcggctg atgacg                                    36

<210> SEQ ID NO 19
<211> LENGTH: 26
<212> TYPE: DNA
<213> ORGANISM: Artificial sequence
<220> FEATURE:
<223> OTHER INFORMATION: Oligonucleotide
<220> FEATURE:
<221> NAME/KEY: Biotin
<222> LOCATION: (1)..(1)
<223> OTHER INFORMATION: Biotin attached to 5' end

<400> SEQUENCE: 19
ccaggcgaaa gggggatgtg ctgcaa                                               26

<210> SEQ ID NO 20
<211> LENGTH: 26
<212> TYPE: DNA
<213> ORGANISM: Artificial sequence
<220> FEATURE:
<223> OTHER INFORMATION: Oligonucleotide

<400> SEQUENCE: 20
tcactcgcgt tgcgttaatt acactc                                               26

<210> SEQ ID NO 21
<211> LENGTH: 24
<212> TYPE: DNA
<213> ORGANISM: Artificial sequence
<220> FEATURE:
<223> OTHER INFORMATION: Oligonucleotide

<400> SEQUENCE: 21
gaggatcccc gggtaccgag ctcg                                                 24

<210> SEQ ID NO 22
<211> LENGTH: 42
<212> TYPE: DNA
<213> ORGANISM: Artificial sequence
<220> FEATURE:
<223> OTHER INFORMATION: Oligonucleotide
<220> FEATURE:
<221> NAME/KEY: Biotin
<222> LOCATION: (1)..(1)
<223> OTHER INFORMATION: Biotin attached to 5' end
<220> FEATURE:
<221> NAME/KEY: Phosphate
<222> LOCATION: (42)..(42)
<223> OTHER INFORMATION: Phosphate attached to 3' end

<400> SEQUENCE: 22
gccgatatcg acaacgccg aactgcgaag ggccaaggct cg                              42

```
<210> SEQ ID NO 23
<211> LENGTH: 26
<212> TYPE: DNA
<213> ORGANISM: Artificial sequence
<220> FEATURE:
<223> OTHER INFORMATION: Oligonucleotide

<400> SEQUENCE: 23
ccaggcgaaa gggggatgtg ctgcaa                                          26

<210> SEQ ID NO 24
<211> LENGTH: 49
<212> TYPE: DNA
<213> ORGANISM: Artificial sequence
<220> FEATURE:
<223> OTHER INFORMATION: 3' phosphate labelled oligo
<220> FEATURE:
<221> NAME/KEY: misc_feature
<223> OTHER INFORMATION: 3' end labelled with phosphate group

<400> SEQUENCE: 24
gccgatatcg gacaacggcc gaactgggaa ggcgcacgga gagaccacg                 49

<210> SEQ ID NO 25
<211> LENGTH: 48
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<223> OTHER INFORMATION: 3' end labelled with phosphate group

<400> SEQUENCE: 25
taggcgtcgg tgacaaacgg ccagctatga cttcgtggtc tctccgtg                  48

<210> SEQ ID NO 26
<211> LENGTH: 25
<212> TYPE: DNA
<213> ORGANISM: Artificial sequence
<220> FEATURE:
<223> OTHER INFORMATION: Primer

<400> SEQUENCE: 26
ggacaacggc cgaactggga aggcg                                           25

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
taggcgtcgg tgacaaacgg ccagc                                           25
```

METHODS AND KITS FOR DETECTING AN ENZYME CAPABLE OF MODIFYING A NUCLEIC ACID

FIELD OF THE INVENTION

The invention relates to methods and kits for detecting an enzyme in a sample, which enzyme is capable of adding or removing a chemical moiety to or from a nucleic acid molecule, thereby conferring the nucleic acid molecule with the ability to be extended to generate a novel detectable nucleic acid molecule.

BACKGROUND TO THE INVENTION

Sensitive methods exist to detect target molecules such as particular nucleic acids, proteins or more simple molecules. The presence of such molecules may be used to indicate an on-going infection or environmental contamination, for example. In prion diseases it would be useful to be able to detect the prion protein where no nucleic acid is present. Also, at certain stages of a viral infection there will be virus antigen present but little viral nucleic acid present. Here it will be useful to be able to detect the viral antigen directly. In order for these methods to be very sensitive and to detect as little as a single molecule the methods must also have high specificity. This high specificity is often achieved by binding two reporters to the target molecule that is to be detected.

In the case of the highly sensitive polymerase chain reaction (PCR), for example, two short nucleic acid probes or primers recognise the target nucleic acid. The detection of the target nucleic acid is thus only achieved when both primers are bound to, and linked through, the same target molecule. Non-specific interactions of the primers with other molecules are not detected unless both primers bind to and are linked by this non-specific interaction. The conditions of the reaction are such that the latter is highly unlikely. The PCR method and other molecular amplification methods, well known in the art, such as Nucleic acid sequence-based amplification (NASBA; Compton, 1991)(1), Transcription Mediated Amplification (TMA; Gen-probe, Inc.) and Self-sustained sequence replication (3SR; Fahy et al., 1991)(2) can be used to detect target nucleic acids.

Immunoassays are often employed in order to detect specific analytes/antigens of interest. Here an antibody, usually a monoclonal antibody, is used in order to allow specific detection of the analyte/antigen. Immuno detection methods can be broadly split into two main categories; solution-based techniques such as enzyme-linked immunosorbent assays (ELISA), immunoprecipitation and immunodiffusion, and procedures such as Western blotting and dot blotting where the samples have been immobilized on a solid support.

Western blot analysis relies on a primary antibody directed against the antigen/analyte, which is added to a membrane containing immobilized antigen/analyte to allow binding to potential antigenic sites. Next, a secondary antibody-enzyme conjugate which recognizes the primary antibody is added in order to find locations where the primary antibody bound. The enzyme, commonly alkaline phosphatase or horseradish peroxidase, conjugated to the secondary antibody can catalyze a reaction with a chemiluminescent substrate in the third step leading to emission of light from the membrane at the reaction site. An x-ray film exposed to the signal provides a visual indication of potential primary antibody recognition. The action of horseradish peroxidase or alkaline phosphatase on a chemiluminescent substrate can give sensitivity down to the picomolar range. Antigens/analytes can be immobilized on nitrocellulose or polyvinylidene fluoride (PVDF) membranes by numerous methods. The ability to detect a given antigen/analyte depends upon the amount of antigen per unit area of the membrane and on the characteristics of the primary antibody.

ELISAs provide sensitive and quantitative detection of specific antigens/analytes. The most common ELISAs are based on an antibody-sandwich format. A sandwich ELISA generally requires two antibodies that are directed against a particular antigen. One antibody is coated onto the wells of the ELISA plate. The wells are then "blocked" using a non specific protein solution (such as milk protein solution) to keep background levels down to a minimum. Samples containing the antigen in solution are then added to the wells and incubated for a sufficient amount of time to allow antigen binding to the immobilized antibody. The second antibody can then bind to the antigen to complete the "sandwich". The second antibody is detected with an enzyme conjugate specific for the second antibody. As an alternative, the second antibody can be labeled itself to allow subsequent detection. When the enzyme substrate is added to the wells in the final step, the conjugated enzyme, which is linked to the antigen, is detected by observing a reaction product which may be calorimetric, fluorescent or chemiluminescent depending on the enzyme and substrate used, using an ELISA plate reader.

The most commonly employed enzymes in immunoassays are horseradish peroxidase (HRP) and alkaline phosphatase (AP). Such enzymes can react with a substrate chromogen to give a coloured product in the presence of an antigen. For example, a substrate chromogen commonly used in conjunction with alkaline phosphatase is 5-bromo, 4-chloro, 3-indolylphosphate (BCIP). An additive such as iodoblue tetrazolium (INT) may also be used to enhance the final colour of the precipitate at the reaction sites, that is where the primary and secondary antibodies have bound to the antigen (which would be a yellow-brown colour for BCIP with INT).

Alkaline phosphatase also has the ability to remove 5' phosphate groups from DNA and RNA. It can also remove phosphates from nucleotides and proteins. These enzymes are most active at alkaline pH. Three major types are commonly employed in immunoassays. Bacterial alkaline phosphatase (BAP) is a highly active enzyme. Calf intestinal alkaline phosphatase (CIP) is purified from bovine intestine, and can be inactivated using protease digestion or heat, for example. Shrimp alkaline phosphatase is derived from a cold-water shrimp and can be inactivated using heat treatment fairly readily.

HRP can be used in a number of bioassays. Peroxidase activity is also present in many cells. Many fluorogenic substrates for HRP are well known in the art and are commercially available. One example is Amplex Red Reagent (Molecular Probes), 10-acetyl-3,7-dihydroxyphenoxazine, which can react with $H_2O_2$ in a 1:1 stochiometry in the presence of HRP to produce highly fluorescent resorufin. An alternative substrate is scopoletin, where HRP catalyzes conversion of the fluorescent scopoletin to a nonfluorescent product. Such substrates are commonly included in ELISA kits to allow detection of sites where an antigen/analyte is present.

Numerous attempts have been made to combine the advantages of immunoassays and nucleic acid amplification techniques. Indirect conjugation methods may be used to link a protein to a nucleic acid molecule. For example, an enzyme such as alkaline phosphatase may be covalently bound to a molecule such as biotin and digoxigenin. This conjugate in turn can then be non-covalently attached to a biotinylated nucleic acid probe via a streptavidin bridge, to be used, for example in Southern and Northern blotting techniques. Such methods can produce consistent results, however the protocols can take much longer than those of direct conjugation methods. Usually several incubation and washing steps are required to bind additional bridging molecules such as streptavidin or an antibody to the labeled probe before the enzyme and substrate can be introduced. Furthermore, with each additional step there is an increased chance of adding background to the signal.

Thus, direct conjugation of an enzyme to a probe is a preferable option, to increase speed and maximise sensitivity. Alkaline phosphatase-conjugated oligonucleotides (Sigma-Genosys) can be used for routine screening applications such as Southern (DNA) and Northern (RNA) blotting, gene mapping and restriction fragment length polymorphism (RFLP) analysis. They can also be used for in situ hybridizations.

Enzyme immunoassays have been established as the most ubiquitous methods for detection of antigen. They are simple, robust and easy to perform. In those cases where extra sensitivity is required more complex and expensive nucleic acid amplification tests such as the Polymerase Chain Reaction (PCR) can be performed.

Numerous attempts have been made to combine the advantages of both approaches. For example, there is use for a sensitive nucleic acid test that can detect antigen. This would be useful in prion detection where there is no associated nucleic acid or in blood bank screening where, at certain times post-infection, there can be virus antigen but little viral nucleic acid.

Previous attempts to combine the immuno and nucleic acid approach by using antibodies labeled with nucleic acids (so-called immuno PCR) have had problems. Linking DNA to antibodies is problematical and the linked DNA is 'sticky' and any unbound DNA is not easily washed from the system prior to detection which can lead to non-specific binding and a high background in the assay.

WO 2005/012567 relates to methods for detecting an enzyme in a sample which is capable of modifying a nucleic acid molecule by detecting the change in the nucleic acid molecule caused by the enzyme. The specific methods disclosed all relate to protection of the nucleic acid molecule from digestion and thus do not detect formation of a new nucleic acid molecule. Thus, the methods, whilst being highly sensitive and efficient methods for detecting a phosphatase enzyme, have as a disadvantage the fact that false positive results may be obtained where the digestion is not 100% efficient. Additionally, if phosphate labelling of the nucleic acid molecule is likewise not 100% efficient this can similarly lead to false positive results.

The present invention overcomes the problems associated with prior art methods as described below.

BRIEF DESCRIPTION OF THE INVENTION AND DEFINITION OF TERMS

The present invention provides improved methods for detecting an enzyme in a sample which is capable of modifying a nucleic acid molecule thereby conferring on the nucleic acid molecule the ability to be extended to generate a novel detectable nucleic acid molecule.

According to a first aspect of the invention there is provided a method of detecting an enzyme in a sample, which enzyme is capable of adding or removing a chemical moiety to or from a nucleic acid molecule, thereby conferring the nucleic acid molecule with the ability to be extended to generate a novel detectable nucleic acid molecule, the method comprising:
    allowing the sample to be tested for the presence of the enzyme to interact with the nucleic acid molecule; and
    testing for interaction of the enzyme with the nucleic acid molecule by detecting the novel nucleic acid molecule generated only in the presence of the enzyme.

The method relies on the fact that if the enzyme is present it will be able to add a chemical moiety to the nucleic acid molecule or remove a chemical moiety from the nucleic acid molecule. This moiety addition or removal confers the nucleic acid molecule with the ability to be extended, for example by polymerisation or ligation to a further nucleic acid molecule, to generate a novel detectable nucleic acid molecule (in a subsequent process). The novel nucleic acid molecule may be detected, thereby allowing a determination of the presence of an enzyme in the sample under test.

Thus, if the enzyme is not present in the sample, the chemical moiety will not be added or removed and thus the nucleic acid molecule will not be susceptible to extension to generate a novel detectable nucleic acid molecule.

The term "chemical moiety" is well known in the art and includes by way of example and not limitation, phosphate groups, carbohydrate groups, nucleotides and acetyl groups etc. Any "chemical moiety" is included within the scope of the invention provided its addition or removal to or from a nucleic acid molecule may be catalysed by an enzyme to thereby confer the nucleic acid molecule with the ability to be extended to generate a novel detectable nucleic acid molecule. The note preferred chemical moieties according to the invention are phosphate groups.

The method is not limited to addition or removal of a single chemical moiety per nucleic acid molecule. The term "a chemical moiety" may, therefore, include multiple copies of the chemical moiety in question.

An "addition" of a chemical moiety may include, by way of example but not limitation, addition of acetyl or phosphate groups. Addition may be at the 5' or 3' end or at any point within the nucleic acid molecule.

A "removal" of a chemical moiety may include, but is not limited to, removal of acetyl and phosphate groups from terminal ends of the nucleic acid molecule or from anywhere along the nucleic acid molecule.

"Extended" is defined herein to include any increase in the length of the nucleic acid molecule when subjected to a further process as compared to the starting, unmodified (in terms of addition or removal of a chemical moiety) nucleic acid molecule. As stated, the extension leads to the generation of a novel detectable nucleic acid molecule.

Examples of "further processes" which may result in extension of the nucleic acid molecule to which the chemical moiety has been added or from which the chemical moiety has been removed include, by way of example and not limitation, ligation and polymerisation. The further process may occur consecutively or simultaneously with the addition or removal of the chemical moiety.

For the avoidance of doubt, it is hereby stated that the novel detectable nucleic acid molecule will have a different overall structure to that of the original nucleic acid molecule. Thus, the novel detectable nucleic acid molecule will contain additional nucleotides such that the novel nucleic acid molecule may be uniquely identified, for example by amplification utilising primers which can only bind and produce an amplification product using the novel nucleic acid molecule as a template. However, it may be that only one strand is extended as compared to the (original) nucleic acid molecule. In certain embodiments, the novel nucleic acid molecule may not be drastically different in structure to the starting nucleic acid molecule. For example, in the case of a nicked nucleic acid molecule (see below), the resultant novel nucleic acid molecule generated according to the invention may simply be an amplified version in which the nicks have been filled in.

Many such additions or removals of chemical moieties which confer on the nucleic acid molecule the ability to be extended (in a subsequent process) to generate a novel detectable nucleic acid molecule are well known in the art, but are not intended to be limiting with respect to the present invention. For example, the addition or removal of a chemical moiety to or from a nucleic acid molecule may allow that molecule to be ligated to a further nucleic acid molecule. Alternatively, for example, the addition or removal of a chemical moiety to or from a nucleic acid molecule may render the nucleic acid molecule susceptible to extension catalysed by a suitable polymerase.

The nucleic acid molecules for use in the methods, and inclusion in the kits, of the invention, must be of sequence and structure such that the enzyme that is being detected in the sample may cause the addition or removal of a chemical moiety to or from the nucleic acid molecule, thereby conferring altered sensitivity on the nucleic acid molecule in a subsequent process. "Nucleic acid" is defined herein to include any natural nucleic acid and natural or synthetic analogues that are capable of being modified by the addition or removal of a chemical moiety to or from a nucleic acid molecule which thereby confers on the nucleic acid molecule the ability to be extended to generate a novel detectable nucleic acid molecule. Suitable nucleic acid molecules may be composed of, for example, double or single-stranded DNA and double or single-stranded RNA. Nucleic acid molecules which are partially double-stranded and partially single-stranded are also contemplated, and indeed are preferred in certain embodiments of the invention, provided the enzyme activity being investigated may add or remove a chemical moiety to or from the nucleic acid molecule. Most preferably the nucleic acid molecules will comprise dsDNA. The term "nucleic acid" encompasses synthetic analogues which are capable of being modified by an enzyme in a sample in an analogous manner to natural nucleic acids, for example nucleic acid analogues incorporating non-natural or derivatized bases, or nucleic acid analogues having a modified backbone. In particular, the term "double-stranded DNA" or "dsDNA" is to be interpreted as encompassing dsDNA containing non-natural bases. Similarly, "dsRNA" is to be interpreted as encompassing dsRNA containing non-natural bases.

According to a preferred embodiment, wherein nucleic acid synthesis is required to generate the novel nucleic acid molecule, the nucleic acid molecule comprises a single stranded DNA molecule which is phosphorylated at the 3' end. In addition, there must be provided a complementary strand to allow assembly of a novel nucleic acid molecule to occur in the situation where the 3' phosphate has been removed. This complementary strand is blocked in order to prevent unwanted nucleic acid synthesis in the absence of phosphatase (which would produce false positive results).

In one specific embodiment, the nucleic acid molecules comprise partially dsDNA. This partially dsDNA is preferably phosphorylated at the 3' ends. The double stranded region is preferably towards the 3' ends of the nucleic acid molecules such that the 3' phosphates are in a double stranded region, while the 5' ends are in a single stranded region. The nucleic acid molecule includes single stranded portions which facilitate priming of nucleic acid synthesis only if the 3' phosphate groups have been removed (as illustrated in FIG. 9).

In a further embodiment, the dsDNA comprises nicked dsDNA. The nicks in the dsDNA expose one or more 3' phosphates at the location of the nicks, which can be acted upon by a phosphatase, if present in the test sample (as illustrated in FIG. 8). The nicks in the DNA may be generated using suitable nicking enzymes.

However, the dsDNA may not necessarily be nicked dsDNA. For example, partially double-stranded DNA may be utilised which may be formed by, for example, the annealing of two 3' phosphate blocked oligonucleotides. The 3' phosphate blocked oligonucleotides may be pre-annealed or may be utilised in the methods of the invention individually, with annealing occurring for example following an initial incubation period.

A "sample" in the context of the present invention is defined to include any sample in which it is desirable to test for the presence of a particular enzyme. Thus the sample may be a clinical sample, or an in vitro assay system for example. The sample may comprise tissue or cells for example.

"Diagnosis" is defined herein to include monitoring the state and progression of the disease, checking for recurrence of disease following treatment and monitoring the success of a particular treatment. The tests may also have prognostic value, and this is included within the definition of the term "diagnosis". The prognostic value of the tests may be used as a marker of potential susceptibility to disease associated with elevated phosphatase levels, for example. Thus, patients at risk may be identified before the disease has a chance to manifest itself in terms of symptoms identifiable in the patient.

ADVANTAGES AND APPLICATIONS OF THE INVENTION

The method of the present invention provides significant technical advantages, due in large part to the fact that a novel nucleic acid molecule is generated as part of the method. For example, background signal, which is a disadvantage of the methods of WO 2005/012567 (as discussed above) is effectively eliminated in the methods of the present invention, due to the fact that an entirely new nucleic acid molecule is generated which can be detected. In particular, the nucleic acid molecule is generated in large quantities according to the preferred embodiments of the invention which aids detection. In the methods of the present invention, unreacted nucleic acid molecule will not contribute to the signal, and as a result no false positive signals are produced when the methods are carried out.

Furthermore, the method is highly sensitive providing detection of an enzyme present down to femtogram and possibly even attogram levels.

The advantages of the present invention include, in certain embodiments, avoiding the use of the 'sticky' DNA-antibody conjugates—in fact the same alkaline phosphatase conjugates can be used that have already been optimized and characterized for many immuno applications. In addition, in the assay there is no need to wash away the DNA as the DNA is used as the target and is only detected when it has been modified and extended to generate a novel detectable nucleic acid molecule. An additional advantage is that immuno PCR can only amplify each DNA target that remains bound to the antigen through the antibody. In the invention described herein, however, the DNA is used as a substrate for antibody bound alkaline phosphatase and each molecule of phosphatase will generate many molecules of detectable DNA target. Thus prior to PCR there has already been an amplification of the DNA target to be detected. This method of two rounds of amplification; one by the antibody-bound enzyme and the second by a nucleic acid amplification method such as PCR gives a much increased sensitivity over that of traditional immuno PCR. There is, therefore, an advantage in providing a method of linking immunoassays and nucleic acid amplification techniques in order to increase the sensitivity of an immunoassay.

Another application of this technique is in the detection of free phosphatase that is important in relation to infectious or non-infectious disease. In infectious diseases, for example, most bacteria or fungi contain bacterially derived or fungally derived phosphatase activity. Normally, such diseases are diagnosed by culture of the infecting organism or by detecting specific antigens, antibodies or the nucleic acid by PCR. However, when the numbers of the infecting organisms are small and the host immunity is compromised (after chemotherapy or in AIDS, for example) it may be very difficult to detect some pathogenic organisms. Infections with aspergillosis is one example where the diagnosis may be difficult. In these cases it may be beneficial to look for the phosphatase associated with the pathogenic organism as this approach is very sensitive; each single organism in the infection having many molecules of phosphatase. It may be appropriate to use an antibody that is specific for the phosphatase associated with the pathogen to first capture that phosphatase before testing in order to remove any host phosphatase (eg anti-phoA has been used to immunocapture the alkaline phosphatase associated with *Mycobacterium smegmatis*; Kriakov et al., (2003) Journal of Bacteriology, 185:983-4991). One approach is to capture the phosphatase associated with the pathogen by using beads coated with the appropriate antibody. After capture and washing of the beads any captured phosphatase may be detected by the method described in this application. It has been observed that many alkaline phosphatases; those from bacteria for example have a very broad substrate specificity which is likely to include dsDNA labelled with end-terminal phosphate (Moura et al., Microbiology. (2001) 147:1525-33).

In a related aspect, the invention provides methods for detecting contaminants, such as toxins, associated with micro-organisms. Contamination of various products for human or animal consumption and use by organisms such as bacteria and yeast represents an important consideration in terms of both safety and economics in a wide range of fields.

For example, water supplies, wastewater, marine environments, pharmaceutical products, cosmetic products, food, beverages, clinical samples including blood and platelet samples etc are all regularly tested for contamination by potentially harmful organisms. Often, the organisms include bacterial and/or yeast species, and these species may produce harmful toxins.

In many cases, tests are carried out based upon measuring the presence of a molecule which can be linked to the presence in the sample of a contaminant or contaminant organism. The present invention allows detection of contaminants to be carried out in a more sensitive manner. This may require use of an antibody or other reagent that specifically binds to the contaminant to first capture that contaminant before utilising the methods of the invention in order to detect rapidly and sensitively the presence of the contaminant. Thus, the antibody or other reagent may be linked to a suitable phosphatase which effectively links antibody binding to the contaminant into the methods of the invention. One approach is to capture the contaminant (possibly associated with a pathogen) by using beads coated with the appropriate antibody or other reagent. After capture and washing of the beads any captured contaminant may be detected by the methods described in this application.

By "contaminant" is meant any substance or molecule which is undesirable in the sample under test. The contaminant will typically have an adverse affect on the properties of the substance which has been contaminated. For example, the contaminant may spoil a foodstuff or may cause illness if the substance is consumed by a human or other animal. Specific examples of contaminants include those produced by micro-organisms. For example, toxins may be detected according to the invention. In one preferred embodiment mycotoxins are tested for. In particular, aflatoxin detection represents a preferred aspect of the invention. These tests are preferably carried out on food samples, where food is defined to include any matter for consumption by humans and/or animals, in particular poultry and livestock.

For the avoidance of doubt, it should be stated that the term "antibody" incorporates all derivatives and variants thereof which retain antigen binding capabilities. Both monoclonal and polyclonal antibodies may be utilised. Derivatised versions, which may be humanized versions of non-human antibodies for example, are also contemplated. Derivatives include, but are not limited to, heavy chain antibodies, single domain antibodies, nanobodies, Fab fragments, scFv etc.

Another application lies in the detection of non-infectious disease. For example, the prostate is a male sex gland which produces fluid that forms part of semen. Cancer of the prostate is one of the most common types of cancer in adult males. Several tests already exist to detect Prostate cancer. Digital rectal examination may be employed to check the surface of the prostate gland. Healthy prostate tissue is typically soft, wheras malignant tissue is firm and is often assymetrical or "stony". Transrectal ultrasounds are also used to measure the size of the prostate and visually identify tumours. Blood tests may also be used in order to check prostate specific antigen (PSA) and prostatic acid phosphatase (PAP) levels. Such tests may confirm a diagnosis made by the examinations mentioned above. PSA is produced by prostate capsule cells and periurethral glands. A highly elevated level of PSA can indicate the presence of prostate cancer. However, the PSA test can produce false positive results in the case of elevated PSA but no cancer, and also false negatives, where PSA levels are not elevated but cancer is present. Because of this, if PSA levels are high a biopsy will usually be carried out by way of confirmation. PAP is an enzyme produced by prostate tissue. The level of PAP increases as prostate disease progresses. One method used in PAP detection is Hillmans method (azo coupling of released naptha-1-ol with a diazonium compound). Lorentz (Continuous monitoring of prostatic acid phosphatase using self-inducing substrates. *Clin Chim Acta.;* 326 (1-2): p 69-80 (December 2002)) discusses a method that allows continuous monitoring of PAP using self-indicating substrates, the preferred substrate being 2-chloro-4-nitrophenyl phosphate (CNP-P).

Alkaline phosphatase is an important enzyme mainly derived from the liver and bones. It is found in lower amounts in the intestines, placenta, kidneys and leukocytes. Serum alkaline phosphatase has also been shown to be present at elevated levels in patients suffering from certain disease conditions. Maldonado et. al (Extremely high levels of alkaline phosphatase in hospitalized patients. *J Clin Gastroenterol.* 27(4): p 342-345 (December 1998) (incorporated herein by reference)) have showed that serum alkaline phosphatase levels are markedly elevated in patients with sepsis, AIDS and malignancies. Wiwanitkit (High serum alkaline phosphatase levels, a study in 181 That adult hospitalized patients. *BMC Family Practice.* 2(1): 2 (July 2002) (incorporated herein by reference)) found high serum alkaline phosphatase levels in patients with obstructive biliary diseases, infiltrative liver diseases, sepsis and cholangiocarcinoma. Serum alkaline phosphatase levels can be readily and sensitively detected according to the methods of the invention and this provides a diagnostic test for a range of conditions.

DETAILED DESCRIPTION OF THE INVENTION

As aforementioned, the present invention seeks to provide improved methods for detecting an enzyme in a sample which is capable of modifying a nucleic acid molecule, by addition or removal of a chemical moiety to or from the nucleic acid molecule, by detecting the change in the nucleic acid molecule caused by the enzyme, the change allowing the nucleic acid molecule to be extended to generate a novel detectable nucleic acid molecule.

Such methods may be employed in a number of settings where a sensitive method of detection of an enzyme activity is required. For example, the methods of the invention may be used to enhance the sensitivity of immunological detection of an analyte and in order to provide more sensitive diagnostic methods for diagnosing specific disease conditions.

Therefore, in a first aspect of the invention there is provided a method of detecting an enzyme in a sample, which enzyme is capable of adding or removing a chemical moiety to or from a nucleic acid molecule, thereby conferring the nucleic acid molecule with the ability to be extended to generate a novel detectable nucleic acid molecule, the method comprising:
  allowing the sample to be tested for the presence of the enzyme to interact with the nucleic acid molecule; and
  testing for interaction of the enzyme with the nucleic acid molecule by detecting the novel nucleic acid molecule generated only in the presence of the enzyme.

In a most preferred embodiment the enzyme will be one which may remove terminal phosphate groups from a nucleic acid molecule. Preferably said enzyme will be a phosphatase which may remove the terminal phosphate group from a nucleic acid molecule. Many phosphatases are well known in the art that may be used in accordance with the invention. The most commonly known phosphatase which has this activity is alkaline phosphatase. Alkaline phosphatase removes phosphate groups from DNA and RNA. It may also remove phosphates from nucleotides and proteins. These enzymes are most active at alkaline pH. Three major types are commonly employed in bioassays, and which may be used in the methods of the invention, although the invention is not limited to use of these specific types. Bacterial alkaline phosphatase (BAP) is a highly active enzyme. Calf intestinal alkaline phosphatase (CIP) is purified from bovine intestine, and may be inactivated using protease digestion or heat, for example. Shrimp alkaline phosphatase is derived from a cold-water shrimp and may be inactivated using heat treatment fairly readily. Further alkaline phosphatase isozymes which may be incorporated into the methods of the invention include, but are not limited to, serum, liver and bone isozymes, and those found in lower amounts in the intestines, placenta, kidneys and leukocytes.

Preferably, the phosphatase will be one capable of removing terminal phosphate groups from the 3' end of a nucleic acid molecule. Examples include alkaline phosphatase and prostatic acid phosphatase, as described above.

Since naturally occurring nucleic acids typically will not contain a phosphate group at the 3' end, in a most preferred embodiment the nucleic acid molecule is a synthesised nucleic acid molecule, preferably an oligonucleotide, which is 3' end labelled with a phosphate group. Synthesized nucleic acid molecules are commercially available and can be made to order with a terminal 3' phosphate group attached. This has the technical advantage that all of the nucleic acid molecules used in the methods of the invention will be labelled with a 3' phosphate group.

According to a preferred "polymerisation" embodiment, wherein nucleic acid synthesis is required to generate the novel nucleic acid molecule, the nucleic acid molecule comprises a single stranded DNA molecule which is phosphorylated at the 3' end. In addition, there must be provided a complementary strand to allow assembly of a novel nucleic acid molecule to occur in the situation where the 3' phosphate has been removed. This complementary strand is blocked in order to prevent unwanted nucleic acid synthesis in the absence of phosphatase (which would produce false positive results). The complementary strand may be blocked by any suitable means, for example, by use of a 3' phosphate group or by incorporation of a dideoxy nucleotide triphosphate (ddNTP) or by using a complementary strand which has a non complementary region (towards or at the 3' end).

In one specific embodiment, the nucleic acid molecules comprise partially dsDNA. This partially dsDNA is preferably phosphorylated at the 3' ends. The double stranded region is preferably towards the 3' ends of the nucleic acid molecules such that the 3' phosphates are in a double stranded region, while the 5' ends are in a single stranded region. The nucleic acid molecule includes single stranded portions which facilitate priming of nucleic acid synthesis only if the 3' phosphate groups have been removed.

An exemplary reaction scheme is shown in FIG. 7. Thus, in the presence of phosphatase, the 3' phosphate present on the single stranded nucleic acid molecule is effectively removed by the action of the phosphatase. This results in a nucleic acid molecule which has the capability of being extended in the presence of a complementary nucleic acid strand. A polymerase can thus direct synthesis of a novel nucleic acid molecule in the presence of the overlapping 3' blocked single stranded DNA molecule. Following this initial "assembly" or "extension" process, the novel nucleic acid molecule may be amplified by any known means in order to sensitively detect the presence of the novel nucleic acid molecule. Because amplification is utilised, the removal of the 3' phosphates does not need to be 100% efficient in order for the method to be effective. Specificity is still assured, since the presence of any 3' phosphates prevents synthesis of a new strand by the polymerase.

Any suitable process may be used for both "assembly" and "amplification" respectively. Suitable techniques are discussed in more detail in the section entitled "preferred detection techniques" below. In particular, preferred polymerases for use in these methods of the invention include Taq, Pfu, Klenow and Vent. Preferably, the polymerases for use in the methods of the invention lack or have a deficiency in their 3'-5' exonuclease activity.

If phosphatase is not present in the sample, the 3' end of the nucleic acid molecule remains phosphorylated. This molecule is, therefore, effectively blocked, so cannot be extended to generate a novel nucleic acid molecule, which is capable of amplification. Thus, the "assembly" or "extension" process does not occur in the absence of phosphatase.

Thus, in one preferred embodiment, the method for detection of a phosphatase comprises the substeps of:
  a) adding to the sample a nucleic acid molecule which comprises a single stranded DNA molecule in which a terminal 3' phosphate is present and an overlapping single stranded DNA molecule which is blocked at the 3' end such that it cannot be extended,
  b) incubating under conditions which permit phosphatase activity c) adding a polymerase to the sample and allowing incubation; and
d) detecting the novel nucleic acid molecule, produced only in the presence of the phosphatase.

By "overlapping" is meant that the nucleic acid strand is complementary in sequence to the other single stranded DNA in the region of overlap (such that base pairing may occur).

In one embodiment, the order of the steps is different. Thus, the overlapping single stranded DNA molecule which is blocked at the 3' end such that it cannot be extended may be added following an incubation with phosphatase.

Accordingly, the method for detection of a phosphatase comprises the substeps of:
a) adding to the sample a nucleic acid molecule which comprises a single stranded DNA molecule in which a terminal 3' phosphate is present,
b) incubating under conditions which permit phosphatase activity,
c) adding an overlapping single stranded DNA molecule which is blocked at the 31 end such that it cannot be extended,
d) adding a polymerase to the sample and allowing incubation; and
e) detecting the novel nucleic acid molecule, produced only in the presence of the phosphatase.

It should be noted that the method may be carried out in real time and all reactants may be pre-mixed rather than following any particular sequence of steps.

In terms of blocking the nucleic acid, as aforementioned, this may be achieved in a number of ways. For example, use of a 3' phosphate group effectively blocks the nucleic acid molecule from being extended, unless there is present a phosphatase in the sample. This type of blocking is useful since, if phosphatase activity is present, it allows the previously blocked nucleic acid molecule to participate in extension and amplification.

Other non-limiting examples of means for blocking the single stranded DNA include incorporation of ddNTPs and also use of DNA molecules which have a small region of non-complementarity with the single stranded DNA molecule in which a terminal 3' phosphate is present. This region of non-complementarity effectively prevents extension of the single stranded DNA.

In a further embodiment, the dsDNA comprises nicked dsDNA. The nicks in the dsDNA expose one or more 3' phosphates at the location of the nicks, which can be acted upon by a phosphatase, if present in the test sample. The nicks in the DNA may be generated using suitable nicking enzymes. Examples include nicking endonucleases such as N.BstNB I, NAlw I, N.BbvC IA, N.BbvC IB and Nb.Bsm I (all available from New England Biolabs). Other commercially available nicking enzymes include N. Bpu10IA (Fermentas AB), Bst9 I, BstNB I (Sibenzyme Limited), N.CviPII and N.CviQXI (Megabase Research Products). Suitable combinations of nicking enzyme may be utilised to nick both strands of a dsDNA molecule as appropriate. For example N.BbvC IA and N.BbvC IB nick on opposite strands within the same overall recognition sequence.

The reaction scheme is shown in FIG. 8. Thus, in the presence of phosphatase, the 3' phosphates present on the nicked strands are effectively removed by the action of the phosphatase. This leaves an entry site for a polymerase on each strand. The polymerase can thus direct synthesis of a complete molecule in which the nicks are effectively filled in. Following this initial "assembly" process, the novel nucleic acid molecule may be amplified by any known means in order to sensitively detect the presence of the novel nucleic acid molecule. Because amplification is utilised, the removal of the 3' phosphates does not need to be 100% efficient in order for the method to be effective. Specificity is still assured, since the presence of any 3' phosphates prevents synthesis of a new strand by the polymerase.

Any suitable process may be used for both "assembly" and "amplification" respectively. Suitable techniques are discussed in more detail in the section entitled "preferred detection techniques" below.

If phosphatase is not present in the sample, the 3' ends of the nicked nucleic acid molecule remain phosphorylated. They are, therefore, effectively blocked, so cannot allow extension catalysed by a suitable polymerase to generate a new nucleic acid strand. Thus, the "assembly" process does not occur in the absence of phosphatase.

Thus, in one preferred embodiment, the method for detection of a phosphatase comprises the substeps of:
a) adding to the sample a nucleic acid molecule which comprises dsDNA with a nick in each strand such that there is present a phosphate group at the 3' end of the DNA at the location of the nick,
b) incubating under conditions which permit phosphatase activity
c) adding a polymerase to the sample and allowing incubation; and
d) detecting the novel nucleic acid molecule, produced only in the presence of the phosphatase.

Preferably, the nicks are offset with respect to one another in the DNA strands. This provides an initiation site for the polymerase on each strand to allow assembly of the novel nucleic acid molecule to take place in the situation where phosphatase is present and the 3' phosphate groups can, therefore, be efficiently removed.

In a closely related embodiment, the dsDNA comprises partially double-stranded DNA. This may be formed by a 3' overlap of two single strands of DNA which are preferably 3' end labelled with phosphate groups. The partially dsDNA may be formed by, for example, the annealing of two 3' phosphate blocked oligonucleotides. The 3' phosphate blocked oligonucleotides may be pre-annealed or may be utilised in the methods of the invention individually, with annealing occurring for example following an initial incubation period.

The reaction scheme is shown in FIG. 9 and differs from that shown in FIGS. 7 and 8 with respect to the exact nature of the starting nucleic acid molecule (although both are partially dsDNA nucleic acid molecules, or at least require some complementarity for extension and amplification to occur). Thus, essentially any dsDNA may be utilised in which terminal 3' phosphates are presented and which has a sufficient single stranded element to allow priming of nucleic acid synthesis if the terminal phosphates are removed by the phosphatase in the sample.

The partially double-stranded DNA cannot be extended by a polymerase unless the blocking phosphate groups at one or both 3' ends have been removed by phosphatase. Removal of the blocking phosphate group(s) by the phosphatase allows the unblocked strand to be extended by a polymerase (prior to or as part of the amplification process) using the complementary strand as a substrate ("assembly"). This, in turn, creates the complementary binding site for a suitable primer such that the extended DNA is now an appropriate substrate for amplification, for example by PCR.

The DNA substrate can be incubated in the presence of the phosphatase as a preformed partially double-stranded DNA substrate (as shown in FIG. 9) or as the individual synthetic oligonucleotides that will form the partially double-stranded DNA in the subsequent annealing step of the PCR. In one embodiment, only one synthetic 3' phosphate blocked oligonucleotide is incubated with the sample, which may contain a phosphatase. Removal of this 3' phosphate allows the generation of an amplification substrate when this oligonucleotide is subsequently mixed with its partially complementary partner included in the amplification incubation and analysis (which may take place in a single step, for example if real-time amplification techniques are utilised). As mentioned above, because amplification is utilised, the removal of the 3' phosphates does not need to be 100% efficient in order for the method to be effective. Specificity is still assured, since the presence of any 3' phosphates prevents synthesis of a new strand by the polymerase.

Any suitable process may be used for both "assembly" and "amplification" respectively. Suitable techniques are discussed in more detail in the section entitled "preferred detection techniques" below.

If phosphatase is not present in the sample, the 3' ends of the nucleic acid molecule(s) remain phosphorylated. They are, therefore, effectively blocked, so cannot allow extension catalysed by a suitable polymerase to generate a new nucleic acid strand. Thus, the "assembly" process does not occur in the absence of phosphatase, and thus a novel nucleic acid molecule is not formed.

Thus, in one preferred embodiment, the method for detection of a phosphatase comprises the substeps of:
a) adding to the sample a nucleic acid molecule which comprises partially dsDNA in which terminal 3' phosphates are present,
b) incubating under conditions which permit phosphatase activity
c) adding a polymerase to the sample and allowing incubation; and
d) detecting the novel nucleic acid molecule, produced only in the presence of the phosphatase.

Thus, the single stranded elements of the partially dsDNA allow priming of nucleic acid synthesis if the terminal 3' phosphates are removed by the phosphatase in the sample.

These "polymerisation" aspects of the invention are particularly preferred due to their inherent simplicity and robust nature. Once the starting material has been provided, namely a suitable DNA substrate having one or more terminal 3' phosphate groups (depending upon the specific embodiment), all that is required is to add suitable components for assembly and amplification to occur. If phosphatase activity is present in the sample under test, the 3' phosphate(s) will be removed and assembly and amplification may occur to generate readily detectable levels of the novel nucleic acid molecule. As shown in the experimental section below (in particular FIG. 11), these "one step" procedures are highly sensitive.

In a further "polymerisation" embodiment, preferably the nucleic acid molecule comprises dsDNA, with a 5' overhang and wherein the shorter strand has a phosphate group attached to the 3' end. Such a nucleic acid molecule is preferably a synthesized nucleic acid molecule.

In one embodiment, the strand producing the 5' overhang incorporates uracil residues in the region of the overhang. Uracil may be present throughout this strand, and may replace thymine residues for example.

Thus, in the presence of phosphatase, the phosphate group will be removed from the 3' end of the shorter strand of the nucleic acid molecule. This then allows the shorter strand of the nucleic acid molecule to act as a primer for nucleic acid synthesis (in the 5' to 3' direction) using the 5' overhang as a template.

If phosphatase is not present in the sample, the 3' end of the shorter strand of the nucleic acid molecule remains phosphorylated and thus is blocked, so cannot act as a primer to be extended to generate a new nucleic acid strand.

Accordingly, the method is preferably carried out by incubating the sample with a polymerase and nucleotides and testing for the presence of the novel nucleic acid molecule following incubation. Preferably, the nucleotides will be dNTPs and, in one preferred embodiment, are labelled so that their incorporation into the newly synthesized strand may be directly detected. Suitable labels include but are not limited to fluorescent labels such as Cy3, Cy5, carboxy-x-rhodamine, 6-JOE etc, radiolabels such as 32P, 33P and 35S and mass labels which allow detection by mass spectroscopy.

Thus, in this embodiment, synthesis of the novel nucleic acid molecule can be directly detected as an indication of the presence of the phosphatase in the sample.

In an alternative embodiment, in which the strand producing the 5' overhang incorporates uracil residues in the overhang the method further comprises incubation with a Uracil N-Glycosylase (UNG). UNG can digest the DNA in which uracil is present, namely in the 5' strand which originally provided the overhang in the nucleic acid molecule. Thus, if phosphatase activity is present, the 3' phosphate on the shorter strand will have been cleaved leading to the extension of this strand in the presence of a suitable polymerase and nucleotides (dNTPs). This polymerisation and digestion of uracil residues in the originally longer strand of the nucleic acid molecule thus leads to generation of a novel single stranded (ss) nucleic acid molecule product, which is then detected to determine the presence of the phosphatase in the sample.

The most preferred method of detection is by amplification using primers which bind to the newly synthesized strand. Unless the 3' phosphate has been removed, the strand extended and the originally longer strand digested, no amplification product will be seen. Thus, the method is both sensitive and selective.

Any polymerase which can catalyse 5' to 3' strand synthesis may be utilised in this embodiment of the invention. For example, the polymerase used may be any one of Taq, Pfu, Vent, Klenow etc.

In one specific embodiment, the method for detection of a phosphatase comprises the substeps of:
a) adding to the sample a nucleic acid molecule which comprises dsDNA with one strand incorporating uracil residues and having a 5' overhang and wherein the shorter strand has a phosphate group at the 3' end
b) incubating under conditions which permit phosphatase activity
c) adding a polymerase, Uracil N-Glycosylase and nucleotides to the sample and allowing incubation; and
d) detecting the novel nucleic acid molecule, produced only in the presence of the phosphatase.

In a further specific embodiment, the method for detection of a phosphatase comprises the substeps of:
a) adding to the sample a nucleic acid molecule which comprises dsDNA with one strand having a 5' overhang and wherein the shorter strand has a phosphate group at the 3' end
b) incubating under conditions which permit phosphatase activity
c) adding a polymerase and labelled nucleotides to the sample and allowing incubation; and
d) detecting the labelled nucleotides incorporated into the novel nucleic acid molecule, produced only in the presence of the phosphatase.

Of course, for all of these "polymerisation" embodiments suitable conditions and reagents for both phosphatase and polymerase activity are ensured. Thus, suitable primers to direct amplification may be designed according to the sequence of the nucleic acid molecule which is to be detected, as is routine for the skilled person and as discussed in more detail hereinbelow. Suitable dNTP mixes etc. may also be supplied as appropriate.

In a further embodiment of the invention, the novel nucleic acid molecule that is detected is generated by ligation of the 3' end of the nucleic acid molecule to the 5' end of a further nucleic acid molecule. In this embodiment, if the phosphatase is present in the sample, it will be able to cleave off the 3' phosphate group from the nucleic acid molecule, leaving an hydroxyl (OH) group at the 3' end of the nucleic acid molecule. Since ligation requires an hydroxyl group at the 3' end of the nucleic acid molecule, if the phosphatase is not present in the sample, the 3' phosphate group will not be cleaved, leaving the nucleic acid molecule blocked from the action of a ligase.

A further nucleic acid molecule is added to the sample which is phosphorylated at the 5' end. Thus, if the phosphate group has been removed from the 3' end of the nucleic acid molecule, this molecule is susceptible to ligation to the 5' phosphorylated end of the further nucleic acid molecule. This ligation reaction is catalyzed by a suitable ligase enzyme present in the sample. Preferred examples are T4 DNA ligase, where the nucleic acid molecule and further nucleic acid molecule are double stranded, and T4 RNA ligase where the nucleic acid molecule and further nucleic acid molecule are single stranded.

Suitable incubation conditions for use of a ligase are well known in the art and are recommended with commercially available ligases.

In one embodiment, both the nucleic acid molecule and further nucleic acid molecule comprise dsDNA with complementary single-stranded overhangs to aid in subsequent ligation. Preferentially the single-stranded overhang is non-palindromic to avoid self-association and possible self ligation. In a further embodiment both the nucleic acid molecule and the further nucleic acid molecule may be blunt ended. In a further embodiment one or both the nucleic acid molecules may be single stranded or partially single stranded DNA or RNA or DNA/RNA hybrid molecules and the ligation catalysed by T4 RNA ligase or other ligase capable of linking single stranded nucleic acids.

The nucleic acid molecule and further nucleic acid molecule are preferably of a different sequence to allow ligation of the nucleic acid molecule and the further nucleic acid molecule to be distinguished from any possible ligation of further nucleic acid molecules to one another.

Preferably, the nucleic acid molecule is not phosphorylated at the 5' end to prevent this ligating to the 3' end of the further nucleic acid molecule. Alternatively, the 3' end of the further nucleic acid molecule may be blocked with a suitable blocking group in order to ensure that it cannot participate in a ligation reaction.

Following ligation, the novel (extended and detectable) ligation product may be detected to determine the presence of the enzyme in the sample. A preferred detection method is nucleic acid amplification using a primer binding to the nucleic acid molecule and a reverse primer binding to the further nucleic acid molecule, as discussed in further detail in the "preferred detection techniques" section below.

As aforementioned, if no enzyme is present in the sample, the phosphate group will remain attached to the 3' end of the nucleic acid molecule. Therefore, this group will act as a blocking group and the ligase will not be able to catalyse ligation, meaning that no novel detectable nucleic acid molecule will be generated.

Preferably, the nucleic acid molecule and further nucleic acid molecule are present in large molar excess over the phosphatase in the sample. Phosphatase may remove 5' terminal phosphates from the further nucleic acid molecule but this is not crucial because provided some further nucleic acid molecule remains it will be able to ligate with nucleic acid molecule from which the 3' phosphate has been removed. This is an important technical distinction over prior art methods. Because a brand new nucleic acid molecule is being detected, only the presence of this molecule in the sample is important. Thus, it is not important if the nucleic acid molecules are present in the sample in excess.

In an alternative "ligation" embodiment, the method additionally involves blocking nucleic acid molecules (as illustrated in FIG. 6). Here the method relies upon the ability of enzymes, such as phosphatases like alkaline phosphatase and prostatic acid phosphatase etc, to remove terminal phosphates that are present at the 51 end of the nucleic acid molecule. Thus, in this embodiment, the nucleic acid molecules are preferably end labelled at the 5' end with phosphate (FIG. 6.A.). Preferably, the nucleic acid molecule is a synthesised nucleic acid molecule, preferably an oligonucleotide, which is 5' end labelled with a phosphate group.

Preferably, the nucleic acid molecule comprises dsDNA, even more preferably ds DNA with a 5' overhang and wherein the overhanging strand has a phosphate group attached at the 5' end. Overhangs in the nucleic acid molecules enhance ligation efficiency and can also be used to ensure specificity of ligation by preventing non-specific ligations occurring.

According to this embodiment, the novel nucleic acid molecule that is detected is generated by ligation of the 31 end of the nucleic acid molecule to the 51 end of a further nucleic acid molecule.

The method is preferably carried out in the presence of a blocking ds nucleic acid molecule which ligates with the 5' end of the nucleic acid molecule in the absence of phosphatase in the sample and thus prevents further ligation to the further nucleic acid molecule to generate the novel detectable nucleic acid molecule.

The detection step is carried out by incubating the sample with a ligase and the blocking double stranded nucleic acid molecule and the further nucleic acid molecule and testing for the presence of the novel nucleic acid molecule following incubation. Preferably, the ligase used is T4 DNA ligase.

The further nucleic acid molecule preferably comprises dsDNA, with a 5' overhang having a phosphate group attached at the 5' end of the overhang. This further nucleic acid molecule is capable of ligating with the nucleic acid molecule in the presence of phosphatase which removes the 5' phosphate from the nucleic acid molecule. The resulting ligation product is a novel product which can be detected to determine the presence of phosphatase in the sample.

Similarly, the blocking nucleic acid molecule preferably comprises dsDNA, with a 5' overhang. In this case, the blocking nucleic acid molecule is not 5' phosphorylated. The blocking nucleic acid molecule is capable of ligating with the nucleic acid molecule in the absence of phosphatase, because the 5' phosphate remains attached to the nucleic acid molecule in the absence of phosphatase. The resulting ligation product blocks ligation of the nucleic acid molecule and the further nucleic acid molecule. This product is different to the novel detectable nucleic acid molecule produced when the nucleic acid molecule and further nucleic acid molecule ligate, so is not detected.

Thus, in this method, added to the sample is a nucleic acid molecule which comprises dsDNA having a 5' overhang at one end and which is phosphorylated at this 5' end. If the phosphatase is present, it will be able to remove the 5' terminal phosphate. Since the blocking nucleic acid molecule does not contain a 5' terminal phosphate either, no ligation is possible between the nucleic acid molecule and the blocking nucleic acid molecule, in the presence of a suitable ligase. Thus, the nucleic acid molecule may ligate to the further nucleic acid molecule, because this nucleic acid molecule has a 5' terminal phosphate group. The resulting novel ligated nucleic acid molecule can be detected, for example by amplification across the ligation boundary, to give an indication of the presence of the enzyme in the sample.

On the other hand, in the absence of phosphatase in the sample, the 5' terminal phosphate will remain attached to the nucleic acid molecule (FIG. 6.B.). Thus, this molecule is susceptible to ligation with the blocking nucleic acid molecule in the presence of a suitable ligase. The resulting ligation product can no longer ligate with the further nucleic acid molecule and thus does not generate a signal. This method is shown schematically in FIG. 6.

Thus, in one specific embodiment, a method is provided for detection of a phosphatase comprising the substeps of:
a) adding to the sample a nucleic acid molecule which comprises dsDNA having a 5' overhang at one end and which is phosphorylated at this 51 end
b) incubating under conditions which permit phosphatase activity
c) adding T4 DNA ligase, a blocking ds nucleic acid molecule which is capable of ligating to the nucleic acid molecule if the 5' phosphate has not been removed from the 5' overhang by phosphatase activity and a further nucleic acid molecule having a 5' overhang at one end and being phosphorylated at this 5' end to the sample and allowing incubation; and
d) detecting the novel ligated nucleic acid molecule, produced only in the presence of the phosphatase, which is the product of ligation of the nucleic acid molecule and the further nucleic acid molecule.

The ligases and polymerases for use with the invention will most preferably be added to the reaction mixture at the same time and in the same reaction mixture as the nucleic acid molecules. Here there is competition between phosphatase activity and ligase or polymerase activity. Phosphatase activity will enable the ligase or polymerase to act upon the nucleic acid molecules included in the reaction mixture. Provided at least some phosphatase activity takes place, this will allow detection of the dephosphorylated nucleic acid molecules because they will be susceptible to ligation or polymerisation to generate a novel detectable nucleic acid molecule. Suitable reaction conditions, which may favour phosphatase activity, may be incorporated in the method in order to achieve this. Thus, in a preferred embodiment, the methods of the invention are carried out in a closed tube format. This is preferably with real-time detection (see below for further details). Such a method provides technical advantages, particularly in a high throughput context, and also minimises sample handling and cross-contamination. Likewise, UNG may be added to the reaction mixture at the same time and in the same reaction mixture as the nucleic acid molecules.

Alternatively, in another embodiment, it may be possible to add the ligase or polymerase (or UNG) enzymes after a suitable amount of time, in a separate reagent addition step, in order to allow any phosphatase present in the test sample to have catalysed removal of terminal phosphates from the nucleic acid molecules in the test sample. A suitable amount of time is defined as one which will allow removal of a sufficient number of phosphates present on nucleic acid molecules to enable the nucleic acid molecule lacking the phosphate group to be detected and distinguished from those nucleic acid molecules which still have a terminal phosphate group attached. For any given assay system the optimal time is determined empirically, by routine experimentation. Preferably substantially all of the nucleic acid molecules are dephosphorylated before the ligase or polymerase are added. Such methods may increase sensitivity of the subsequent detection because more nucleic acid molecules will have had time to be dephosphorylated by phosphatase activity before the ligases or polymerases have the opportunity to act on the nucleic acid molecules. However, since the phosphatase activity actually allows the ligase or polymerase respectively to act on the nucleic acid molecule, there is no absolute requirement to wait. This is an important technical advantage of the methods of the present invention, since in previously disclosed methods phosphatase activity had to be sufficiently efficient to protect the nucleic acid molecules from digestion, otherwise no signal would be generated. This makes the present methods more robust.

In a further embodiment, the ligase or polymerase (or UNG) may be included in the initial test sample together with the nucleic acid molecules, however they may be specifically inhibited initially in order to allow the phosphatase, if present, to remove a phosphate moiety from the nucleic acid molecules. Following a suitable period to allow phosphatase activity to remove the terminal phosphates from the nucleic acid molecules, the ligase or polymerase may be activated by removing the inhibitory conditions. The suitable conditions will be well known to one of skill in the art and are listed with commercially available enzymes and thus may be readily incorporated into the methods of the present invention.

Preferred Nucleic Acid Molecules

Preferably, in the methods of the invention, the nucleic acid molecules are synthesised nucleic acid molecules. This ensures there is 100% efficiency of phosphate labelling.

In a preferred embodiment, relating to the first ligation embodiment (FIG. 4), the nucleic acid molecule will comprise ss or dsDNA. In further embodiments the dsDNA will have a single-stranded region that is complementary to the further nucleic acid but blunt ended molecules may be used. The further nucleic acid molecule will be complementary to the nucleic acid molecule in that either both will be ss or both will be ds with complementary single stranded overhangs. This allows them to be ligated together provided phosphatase is present to remove the 3' terminal phosphate from the nucleic acid molecule (FIG. 4.A. no phosphatase added; FIG. 4.B. phosphatase added). The further nucleic acid molecule is labelled at the 5' end with a phosphate group. If the further nucleic acid molecule is ds, preferably only one 5' end has a phosphate group attached.

In the alternative, the dsDNA further nucleic acid molecule may be produced using amplification techniques such as PCR (FIG. 5.A. no phosphatase added; FIG. 5.B. phosphatase added). In this embodiment the PCR is most preferably performed using two primers that have 5' phosphate groups. In order to ensure that the PCR product is phosphorylated it is also preferred, as an additional step, to treat the dsDNA with a kinase such as polynucleotide kinase prior to use.

In a still further embodiment the dsDNA further nucleic acid molecule may be produced from a plasmid. If a plasmid is cut with a restriction enzyme that leaves blunt ends, linear blunt ended nucleic acid molecules will be produced having 5' phosphate moieties at both ends. Any length of nucleic acid molecule may be used in the methods of the invention, provided that the addition or removal of a chemical moiety to or from the nucleic acid molecule caused by the enzyme in the sample confers on the nucleic acid molecule the ability to be extended (in a subsequent process) to produce a novel nucleic acid molecule which is capable of being detected.

As discussed above, in the further ligation embodiment, involving blocking nucleic acid molecules, the nucleic acid molecules are preferably double stranded (ds) (FIG. 6). These ds nucleic acid molecules preferably contain complementary overhanging strands which allow ligation in the presence of a ligase depending upon whether a phosphatase is present in the sample or not. Here suitable overhangs may be produced by synthesising nucleic acid molecules in an appropriate manner. Alternatively, for example, suitable overhangs can be produced by utilising nucleic acid molecules containing suitable restriction enzyme sites, such that cleavage with a restriction enzyme can generate an appropriate overhang. The design of such nucleic acid molecules would be familiar and routine for one of skill in the art (see the experimental section for example). Suitable restriction enzymes are extremely well characterized and are commercially available.

As discussed above, for one polymerase embodiment, the nucleic acid molecule may be double stranded with a 5' overhang. Preferably, the 3' end of the shorter strand is phosphorylated and the 5' longer strand incorporates uracil residues.

According to a preferred embodiment, wherein nucleic acid synthesis is required to generate the novel nucleic acid molecule, the nucleic acid molecule comprises a single stranded DNA molecule which is phosphorylated at the 3' end. In addition, there must be provided a complementary strand to allow assembly of a novel nucleic acid molecule to occur in the situation where the 3' phosphate has been removed. This complementary strand is blocked in order to prevent unwanted nucleic acid synthesis in the absence of phosphatase (which would produce false positive results). The complementary strand may be blocked by any suitable means.

In one specific embodiment, the nucleic acid molecules comprise partially dsDNA. This partially dsDNA is preferably phosphorylated at the 3' ends. The double stranded region is preferably towards the 3' ends of the nucleic acid molecules such that the 3' phosphates are in a double stranded region, while the 5' ends are in a single stranded region. The nucleic acid molecule includes single stranded portions which facilitate priming of nucleic acid synthesis only if the 3' phosphate groups have been removed.

In a further embodiment, the dsDNA comprises nicked dsDNA. The nicks in the dsDNA expose one or more 3' phosphates at the location of the nicks, which can be acted upon by a phosphatase, if present in the test sample. The nicks in the DNA may be generated using suitable nicking enzymes.

However, the dsDNA may not necessarily be nicked dsDNA. For example, partially double-stranded DNA may be utilised which may be formed by, for example, the annealing of two 3' phosphate blocked oligonucleotides. The 3' phosphate blocked oligonucleotides may be pre-annealled or may be utilised in the methods of the invention individually, with annealing occurring for example following an initial incubation period.

Preferred Detection Techniques

In order to make the technique maximally sensitive the novel nucleic acid molecule generated as a result of the addition or removal of a chemical moiety to or from the nucleic acid molecule may be detected with the use of nucleic acid amplification techniques. Such amplification techniques are well known in the art, and include methods such as PCR, NASBA (Compton, 1991), 3SR (Fahy et al., 1991), Rolling circle replication and Transcription Mediated Amplification (TMA). Amplification is achieved with the use of amplification primers specific for the sequence of the novel nucleic acid which is to be detected. In order to provide specificity for the nucleic acid molecules primer binding sites corresponding to a suitable region of the sequence may be selected. The skilled reader will appreciate that the nucleic acid molecules may also include sequences other than primer binding sites which are required for detection of the change in the nucleic acid molecule caused by the enzyme in the sample, for example RNA Polymerase binding sites or promoter sequences may be required for isothermal amplification technologies, such as NASBA, 3SR and TMA. Primer binding sites may bridge the nucleic acid molecule and further nucleic acid molecule ligation boundary such that an amplification product is only generated if ligation has occurred, for example.

It should be noted that whilst PCR is a preferred amplification method, to include variants on the basic technique such as nested PCR, equivalents may also be included within the scope of the invention. Examples include isothermal amplification techniques such as NASBA, 3SR, TMA and triamplification, all of which are well known in the art and commercially available. Other suitable amplification methods include the ligase chain reaction (LCR) (Barringer et al, 1990), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995) and nick displacement amplification (WO2004/067726).

TMA (Gen-probe Inc.) is an RNA transcription amplification system using two enzymes to drive the reaction, namely RNA polymerase and reverse transcriptase. The TMA reaction is isothermal and may amplify either DNA or RNA to produce RNA amplified end products. TMA may be combined with Gen-probe's Hybridization Protection Assay (HPA) detection technique to allow detection of products in a single tube. Such single tube detection is a preferred method for carrying out the invention. The list above is not intended to be exhaustive. Any nucleic acid amplification technique may be used provided the appropriate nucleic acid product is specifically amplified.

Thus, in a preferred aspect of the invention the method of the invention is carried out using nucleic acid amplification techniques in order to detect the novel nucleic acid molecule produced as a direct result of the addition or removal of a chemical moiety which renders the nucleic acid molecule susceptible to extension. In a preferred embodiment the technique used is selected from PCR, NASBA, 3SR and TMA.

Detection of the amplification products may be by routine methods, such as, for example, gel electrophoresis but is preferably carried out using real-time detection methods.

A number of techniques for real-time detection of the products of an amplification reaction are known in the art. Many of these produce a fluorescent read-out that may be continuously monitored; specific examples being MOLECULAR BEACONS and fluorescent resonance energy transfer probes. Real-time techniques are advantageous because they keep the reaction in a "single tube". This means there is no need for downstream analysis in order to obtain results, leading to more rapidly obtained results. Furthermore keeping the reaction in a "single tube" environment reduces the risk of cross contamination and allows a quantitative output from the methods of the invention. This may be particularly important in the diagnostic setting outlined below. Real-time quantitation of PCR reactions may be accomplished using the TAQ- MAN® system (Applied Biosystems), see Holland et al; Detection of specific polymerase chain reaction product by utilising the 5'-3' exonuclease activity of *Thermus aquaticus* DNA polymerase; *Proc. Natl. Acad. Sci. USA* 88, 7276-7280 (1991), Gelmini et al. Quantitative polymerase chain reaction-based homogeneous assay with fluorogenic probes to measure C-Erb-2 oncogene amplification. *Clin. Chem.* 43, 752-758 (1997) and Livak et al. Towards fully automated genome wide polymorphism screening. *Nat. Genet.* 9, 341-342 (19995) incorporated herein by reference). TAQMAN® probes are widely commercially available, and the TAQMAN® system (Applied Biosystems) is well known in the art. TAQMAN® probes anneal between the upstream and downstream primer in a PCR reaction. They contain a 5'-fluorophore and a 3'-quencher. During amplification the 5'-3' exonuclease activity of the Taq polymerase cleaves the fluorophore off the probe. Since the fluorophore is no longer in close proximity to the quencher, the fluorophore will be allowed to fluoresce. The resulting fluorescence may be measured, and is in direct proportion to the amount of target sequence that is being amplified.

In the MOLECULAR BEACON system, see Tyagi & Kramer. MOLECULAR BEACONS—probes that fluoresce upon hybridization. *Nat. Biotechnol.* 14, 303-308 (1996) and Tyagi et al. Multicolor MOLECULAR BEACONS for allele discrimination. *Nat. Biotechnol.* 16, 49-53 (1998) (incorporated herein by reference), the beacons are hairpin-shaped probes with an internally quenched fluorophore whose fluorescence is restored when bound to its target. The loop portion acts as the probe while the stem is formed by complimentary "arm" sequences at the ends of the beacon. A fluorophore and quenching moiety are attached at opposite ends, the stem keeping each of the moieties in close proximity, causing the fluorophore to be quenched by energy transfer. When the beacon detects its target, it undergoes a conformational change forcing the stem apart, thus separating the fluorophore and quencher. This causes the energy transfer to be disrupted to restore fluorescence.

Any suitable fluorophore is included within the scope of the invention. Fluorophores that may possibly be used in the method of the invention include, by way of example, FAM, HEX™, NED™, ROX™, Texas Red™ etc. Quenchers, for example Dabcyl and TAMRA are well known quencher molecules that may be used in the method of the invention. However, the invention is not limited to these specific examples.

A further real-time fluorescence based system which may be incorporated in the methods of the invention is Zeneca's SCORPION system, see Detection of PCR products using self-probing amplicons and fluorescence by Whitcombe et al. Nature Biotechnology 17, 804-807 (1 Aug. 1999). This reference is incorporated into the application in its entirety. The method is based on a primer with a tail attached to its 5' end by a linker that prevents copying of the 5' extension. The probe element is designed so that it hybridizes to its target only when the target site has been incorporated into the same molecule by extension of the tailed primer. This method produces a rapid and reliable signal, because probe-target binding is kinetically favoured over intrastrand secondary structures.

Additional real-time detection techniques which are well known to those skilled in the art and which are commercially available include LIGHTCYCLER® technology and AMPLIFLUOUR® primer technology.

Thus, in a further aspect of the invention the products of nucleic acid amplification are detected using real-time techniques. In one specific embodiment of the invention the real-time technique consists of using any one of the TAQMAN® system, LIGHTCYCLER® system, AMPLIFLUOUR® system, the MOLECULAR BEACONS® system or the SCORPION® probe system.

In a most preferred embodiment the reaction mixture contains all of; the sample under test, the nucleic acid molecule and overlapping single stranded DNA molecule which is blocked at the 3' end or nicked dsDNA molecule or particularly dsDNA in which 3' terminal phosphate groups are present, the required polymerase, nucleotides (which may be labelled if required) and all reagents, buffers and any other enzymes required for amplification of the novel nucleic acid molecule in addition to the reagents required for real-time detection of the novel nucleic acid molecule. This is relevant to the most preferred "polymerisation" embodiments.

In an alternative embodiment, the reaction mixture contains all of the sample under test, the nucleic acid molecule and further nucleic acid molecule, the required ligase and all reagents, buffers and enzymes required for amplification of the novel ligated nucleic acid molecule in addition to the reagents required to allow real time detection of amplification products. Alternatively, the reaction mixture contains all of; the sample under test, the nucleic acid molecule (as defined above), the required polymerase, nucleotides and optionally UNG, and all reagents, buffers and enzymes required for amplification of the novel extended nucleic acid molecule in addition to the reagents required to allow real time detection of amplification products. Thus the entire detection method for the enzyme of interest, most preferably a phosphatase, occurs in a single reaction, with a quantitative output, and without the need for any intermediate washing steps. Use of a "single tube" reaction is advantageous because there is no need for downstream analysis in order to obtain results, leading to more rapidly obtained results. Furthermore keeping the reaction in a "single tube" environment reduces the risk of cross contamination and allows a quantitative output from the methods of the invention. Also, single tube reactions are more amenable to automation, for example in a high throughput context.

Alternatively the method of the invention may be carried out in step-wise fashion. Thus, the nucleic acid molecules may be added first to the sample under test, allowing any enzyme present in the sample to add a chemical moiety to or remove a chemical moiety from the nucleic acid molecule. Following this, in alternative embodiments, the ligase or polymerase (possibly also with UNG) enzymes may be added to ligate the nucleic acid molecule and the further nucleic acid molecule or to extend the nucleic acid molecule. This may involve changing the reaction conditions in the sample. The ligase or polymerase (possibly with UNG) may then, in a further embodiment, be inactivated before adding reagents necessary for detection, which will most preferably be by amplification. Depending on whether an isothermal amplification technique is used this may influence whether the ligases or polymerase (possibly with UNG) will need to be inactivated before carrying out the detection step. If real time detection is being utilised the required reagents are added together with the reagents required for the amplification stage.

Primers specific for the novel detectable nucleic acid molecule to be amplified are utilised in the methods and kits of the invention. Any primer that may direct sequence specific amplification of the novel detectable nucleic acid molecule with minimum background, non-specific amplification, may be utilised. Primers may comprise DNA or RNA and synthetic equivalents depending upon the amplification technique being utilised. For example for standard PCR a short single stranded DNA primer pair tends to be used, with both primers bordering a region of interest to be amplified. The types of primers that may be used in nucleic acid amplification technology such as PCR, 3SR, NASBA and TMA are well known in the art.

Suitable probes for use in the real-time methods may also be designed, in order that they may be used in conjunction with the nucleic acid molecules in the methods of the invention. Thus, for example, when using the TAQMAN® technique, the probes may need to be of sequence such that they can bind between primer binding sites on the nucleic acid molecule which is modified by an enzyme to give the change that is subsequently detected in real-time. Similarly MOLECULAR BEACON probes may be designed that bind to a relevant portion of the nucleic acid sequence incorporated into the methods and kits of the invention. If using the SCORPION probe technique for real time detection the probe will need to be designed such that it hybridizes to its target only when the target site has been incorporated into the same molecule by extension of the tailed primer. AMPLIFLUOUR technology will require suitable design of the primers, but does not require a separate probe. Therefore, the invention further provides for inclusion of probes or suitably designed primers, for use in real-time detection methods in the present invention.

Alternative techniques may be used to detect the addition of a chemical moiety to, or removal of a chemical moiety from, the nucleic acid molecule, which ultimately leads to the generation of a novel detectable nucleic acid molecule. Examples of alternative detection techniques include mass spectrometry, including matrix assisted laser desorption (MALDI) mass spectrometry and MALDI-Time of Flight (MALDI-TOF) mass spectrometry, chromatography and use of microarray technology (Motorola, Nanogen). Mass spectrometry will allow the expected molecular weight of the novel nucleic acid molecules to be accurately measured. MALDI-TOF relies upon a high voltage potential which rapidly extracts ions and accelerates them down a flight tube. A detector at the end of the flight tube is used to determine the time elapsed from the initial laser pulse to detection of the ions. The flight time is proportional to the mass of the ion. Thus, in the method of the invention the difference in the mass of the nucleic acid molecules compared to the novel detectable nucleic acid molecule is sufficient to allow specific and sensitive detection.

Similarly, by using a microarray with suitable probes attached to the solid support, the novel nucleic acid molecules produced in the methods of the invention may be identified in a downstream process.

These alternative techniques may preferably be used in conjunction with nucleic acid amplification techniques in order to characterise the amplification products. This will help to remove false positive results, where an amplified product had been produced which is not the expected product. Thus the advantages of an amplification step to increase sensitivity is combined with a step to accurately characterise the amplification products thus making the methods of the invention even more accurate.

Use of polymerases lacking or having reduced 5'-3' exonuclease activity may be preferable in any of the embodiments of the invention. Taq or Klenow exo-polymerases may be utilised for example, in particular in the polymerisation embodiments in which detection is carried out in a single "extension" or "assembly" and amplification step.

Immunoassays

In a particular embodiment the methods of the invention can be used to enhance the sensitivity of any assay system which is based upon detection of phosphatase activity. In a preferred embodiment the method of the invention may advantageously be used to enhance the sensitivity of an immunoassay, such as a Western blot, dot blot, ELISA, immunoprecipitation or immunodiffusion for example. However, the invention is not intended to be restricted to only these examples.

In many immunoassays a primary antibody will be used which is specific for the antigen to be detected. In order to detect binding of the first, typically unlabelled, antibody to the antigen, following a washing step to remove unbound antigen, a secondary antibody will be added which cross reacts with the primary antibody. This secondary antibody is often conjugated to an enzyme such as horseradish peroxidase or alkaline phosphatase. Alternatively, for solution-based assays such as ELISAs, immunoprecipitation and immunodiffusion the secondary antibody recognises a second site on the antigen. Again, the secondary antibody is often conjugated to an enzyme such as HRP or AP. Such enzymes can react with a substrate chromogen to give a coloured product in the presence of an antigen. For example, a commonly used substrate chromogen used with alkaline phosphatase is 5-bromo, 4-chloro, 3-indolylphosphate (BCIP). An additive such as iodoblue tetrazolium (INT) may also be used to enhance the final colour of the precipitate at the reaction sites, that is where the primary and secondary antibodies have bound to the antigen (which is a yellow-brown colour for BCIP with INT). Many fluorogenic substrates for HRP are well known in the art and are commercially available. One example is Amplex Red Reagent (Molecular Probes), 10-acetyl-3,7-dihydroxyphenoxazine, which can react with $H_2O_2$ in a 1:1 stochiometry in the presence of HRP to produce highly fluorescent resorufin. An alternative substrate is scopoletin, where HRP catalyzes conversion of the fluorescent scopoletin to a nonfluorescent product. Such substrates are commonly included in ELISA kits to allow detection of sites where an antigen/analyte is present.

The inventors have utilised the fact that enzymes commonly used in immunoassays, such as alkaline phosphatase, can also act upon nucleic acid substrates to give a detectable change. Phosphatases, such as calf intestinal phosphatase (CIP) for example, may remove terminal phosphate groups from a nucleic acid molecule such as a double stranded DNA (dsDNA) molecule. Any phosphatase capable of such activity is included within the scope of the present invention. By including suitable nucleic acid molecules in the immunoassay, the presence of an analyte/antigen may be detected in a sensitive manner by detecting the novel nucleic acid molecule generated as a consequence of the (antibody conjugated) enzyme which is capable of either adding or removing a chemical moiety to or from the nucleic acid molecule, which thus means the nucleic acid molecule can be extended to generate a novel nucleic acid molecule.

Thus in one preferred embodiment the method of the invention is carried out to detect the presence of an enzyme wherein the enzyme is one which is used for detection of an antigen/analyte in an immunoassay. Preferably, the enzyme that is detected is attached to an antibody which is used in the detection of an antigen/analyte. The antibody may be a primary antibody or a secondary antibody.

However, the method of the invention is not limited to use for enhancing the sensitivity of immunoassays. As aforementioned Alkaline phosphatase-conjugated oligonucleotides/probes (Sigma-Genosys) may be used for routine screening applications such as Southern (DNA) and Northern (RNA) blotting, gene mapping and restriction fragment length polymorphism (RFLP) analysis. They may also be used for in situ hybridizations. The methods of the present invention may be utilised to enhance the sensitivity of such techniques. Instead of using calorimetric detection of alkaline phosphatase (AP) activity the method of the present invention may be used in order to detect AP activity and thus probe binding. By coupling AP's ability to modify a nucleic acid molecule to an amplification step to detect the novel nucleic acid molecule generated according to the methods described above, sensitivity is increased. Care will need to be taken to ensure that the oligonucleotides conjugated to the AP molecules will not interfere with the detection of the nucleic acid molecule being modified by AP. Also the actual nucleic acid sequences being probed may need to be treated to prevent interference with the method of the invention. For example, ligation and polymerisation can be prevented by ensuring the molecules are blocked and can not participate in the reaction. Suitable blocking techniques are discussed in greater detail above.

The combination of immunoassays and the methods of the present invention is particularly applicable to detection of certain contaminants or toxins, for example in foods (see the section entitled "DETECTION OF CONTAMINANTS" below).

Immobilization of Components

In one aspect of the invention, the methods of the invention are carried out wherein the enzyme to be detected and/or the nucleic acid molecule and/or the further nucleic acid molecule and/or the blocking nucleic acid molecule are immobilized on separate binding entities capable of interacting with one another either directly or indirectly.

Such immobilization to binding entities which can bind to one another directly or indirectly may allow the components of the methods to be brought into proximity, thus enhancing the sensitivity of the methods still further. Suitable binding entities include antibodies binding to antigens, and streptavidin/biotin conjugate pairs (see the experimental section below).

This kind of immobilization is especially relevant in the methods and kits used to detect infectious agent phosphatase wherein the phosphatase from the infectious agents must be separated from the host cell phosphatases before detection using a suitable antibody (see section "DETECTION OF INFECTIOUS DISEASE" below) and also in the detection of certain contaminants or toxins, for example in foods (see the section entitled "DETECTION OF CONTAMINANTS" below).

Detection of Infectious Disease

As aforementioned, the method of the invention may be applied to detect free phosphatase associated with an infectious agent.

Thus, there is provided a method of detecting a phosphatase from an infectious agent in a sample wherein the phosphatase is capable of adding or removing a chemical moiety to or from a nucleic acid molecule, thereby conferring the nucleic acid molecule with the ability to be extended to generate a novel detectable nucleic acid molecule, the method comprising:

allowing the sample to be tested for the presence of the phosphatase to interact with the nucleic acid molecule; and testing for interaction of the phosphatase with the nucleic acid molecule by detecting the novel nucleic acid molecule generated only in the presence of the phosphatase, wherein detection of the novel nucleic acid molecule indicates the presence of the infectious agent.

In one embodiment the infectious agent is *Aspergillus* or *Staphyloccocus* species.

The sample will generally be one taken from a subject suspected of being infected by the infectious agent. Any type of sample may be used in which the infectious agent may be present. Tissue and cell samples will generally be utilised although whole blood, serum, plasma, urine, chyle, stool, ejaculate, sputum, nipple aspirate, saliva etc. taken from a subject may also be tested in the method.

The subject is most preferably a human subject, but may include an animal subject such as a dog, cat, pig, cow or monkey for example.

The method is intended to be an in vitro method utilising an isolated sample. However, in one embodiment the method may additionally comprise the step of obtaining a suitable sample from the subject under test.

In a preferred embodiment, and in order to ensure that phosphatase enzyme associated with an infectious agent is distinguished from host phosphatase enzyme, the method additionally comprises the substeps of:
 a) capture and separation of the infectious agent-specific phosphatase via a specific antibody
 b) adding to the separated phosphatase a nucleic acid molecule which comprises ss or dsDNA which is phosphorylated at a 3' end
 c) incubating under conditions which permit phosphatase activity
 d) adding a ligase and a further nucleic acid molecule having a 5' terminal phosphate group attached to the sample and allowing incubation; and
 e) detecting the novel ligated nucleic acid molecule, wherein the presence of the novel ligated nucleic acid molecule indicates the presence of the infectious agent phosphatase.

If the nucleic acid molecule and further nucleic acid molecule are ss, preferably the ligase is T4 RNA ligase and if the nucleic acid molecule and further nucleic acid molecule are ds, preferably with non-palindromic single stranded overhangs (see above), preferably the ligase is T4 DNA ligase.

In an equally preferred embodiment, the method for detection of a phosphatase enzyme associated with an infectious agent comprises the substeps of:
 a) capture and separation of the infectious agent-specific phosphatase via a specific antibody
 b) adding to the separated phosphatase a nucleic acid molecule which comprises dsDNA with one strand having a 5' overhang and wherein the shorter strand has a 3' terminal phosphate group attached
 c) incubating under conditions which permit phosphatase activity
 d) adding a polymerase and labelled nucleotides to the sample and allowing incubation; and
 e) detecting the labelled nucleotides incorporated into the novel nucleic acid molecule, wherein the presence of the labelled nucleotides in the novel nucleic acid molecule indicates the presence of the infectious agent phosphatase.

In a further embodiment, the method for detection of a phosphatase enzyme associated with an infectious agent comprises the substeps of:
 a) capture and separation of the infectious agent-specific phosphatase via a specific antibody
 b) adding to the separated phosphatase a nucleic acid molecule which comprises dsDNA with one strand having a 5' overhang and which incorporates uracil residues and wherein the shorter strand has a 3' terminal phosphate group attached
 c) incubating under conditions which permit phosphatase activity d) adding a polymerase, Uracil N-Glycosylase (UNG) and nucleotides to the sample and allowing incubation; and
e) detecting the novel nucleic acid molecule, wherein the presence of the novel nucleic acid molecule indicates the presence of the infectious agent phosphatase.

In a still further embodiment, the method according to the invention for detection of a phosphatase enzyme associated with an infectious agent comprises the substeps of:
a) capture and separation of the infectious agent-specific phosphatase via a specific antibody
b) adding to the separated phosphatase a nucleic acid molecule which is phosphorylated at an overhanging 5' end
c) incubating under conditions which permit phosphatase activity
d) adding a ligase, a blocking ds nucleic acid molecule which is capable of ligating to the nucleic acid molecule if the 5' phosphate has not been removed from the 5' overhang by phosphatase activity and a further nucleic acid molecule having a 5' overhang at one end and being phosphorylated at this 5' end to the sample and allowing incubation; and
e) detecting the novel ligated nucleic acid molecule, produced only in the presence of the phosphatase, which is the product of ligation of the nucleic acid molecule and the further nucleic acid molecule, wherein the presence of the novel ligated nucleic acid molecule indicates the presence of the infectious agent phosphatase.

In a particularly preferred embodiment, the method for detection of a phosphatase enzyme associated with an infectious agent comprises the substeps of:
a) capture and separation of the infectious agent-specific phosphatase via a specific antibody
b) adding to the sample a nucleic acid molecule which comprises a single stranded DNA molecule in which a terminal 3' phosphate is present and an overlapping single stranded DNA molecule which is blocked at the 3' end such that it cannot be extended,
c) incubating under conditions which permit phosphatase activity
d) adding a polymerase to the sample and allowing incubation; and
e) detecting the novel nucleic acid molecule, wherein the presence of the novel nucleic acid molecule indicates the presence of the infectious agent phosphatase.

In a related embodiment, the order of the steps is different. Thus, the overlapping single stranded DNA molecule which is blocked at the 3' end such that it cannot be extended may be added following an incubation with phosphatase.

Accordingly, the method for detection of a phosphatase enzyme associated with an infectious agent comprises the substeps of:
a) capture and separation of the infectious agent-specific phosphatase via a specific antibody
b) adding to the sample a nucleic acid molecule which comprises a single stranded DNA molecule in which a terminal 3' phosphate is present,
c) incubating under conditions which permit phosphatase activity
d) adding an overlapping single stranded DNA molecule which is blocked at the 3' end such that it cannot be extended,
e) adding a polymerase to the sample and allowing incubation; and
f) detecting the novel nucleic acid molecule, wherein the presence of the novel nucleic acid molecule indicates the presence of the infectious agent phosphatase.

In another preferred embodiment, the method for detection of a phosphatase enzyme associated with an infectious agent comprises the substeps of:
a) capture and separation of the infectious agent-specific phosphatase via a specific antibody
b) adding to the sample a nucleic acid molecule which comprises partially dsDNA in which terminal 3' phosphates are present,
c) incubating under conditions which permit phosphatase activity
d) adding a polymerase to the sample and allowing incubation; and
e) detecting the novel nucleic acid molecule, wherein the presence of the novel nucleic acid molecule indicates the presence of the infectious agent phosphatase.

Thus, the single stranded elements of the partially dsDNA allow priming of nucleic acid synthesis if the terminal 3' phosphates are removed by the phosphatase in the sample.

Preferably, the dsDNA comprises partially double-stranded DNA formed by a 3' overlap of the two single strands of DNA.

In a different embodiment, the nucleic acid molecule comprises dsDNA with a nick in each strand (as discussed in more detail supra).

For the avoidance of doubt, it is hereby stated that steps b) to e) of the various methods may be carried out at the same time (see above), and in a single tube (real time) format.

For the diagnostic methods referred to in this section, the features of the method of the invention, set out in more general terms above, apply equally (and are not repeated for reasons of conciseness).

Detection of Contaminants

As aforementioned, the method of the invention may be applied to detect contaminants or other toxins which may be found in certain samples. For example, levels of toxins in foodstuffs is particularly relevant, both for human and animal, in particular poultry and livestock consumption. In other examples, water supplies, wastewater, marine environments, pharmaceutical products, cosmetic products, beverages, clinical samples including blood and platelet samples etc are all regularly tested for contamination by potentially harmful organisms. Often, the organisms include bacterial and/or yeast species, and these species may produce harmful toxins.

This aspect of the invention may combine immunoassays with the methods of the invention in a preferred embodiment.

Thus, there is provided a method of detecting a contaminant in a sample the method comprising:
a) capture and separation of the contaminant via a specific binding reaction involving a reagent capable of specifically binding to the contaminant, wherein the reagent is linked to an enzyme which is capable of adding or removing a chemical moiety to or from a nucleic acid molecule, thereby conferring the nucleic acid molecule with the ability to be extended to generate a novel detectable nucleic acid molecule,
b) adding to the captured and separated contaminant the nucleic acid molecule
c) incubating under conditions which permit enzyme activity; and
d) testing for interaction of the enzyme with the nucleic acid molecule by detecting the novel nucleic acid molecule generated only in the presence of the enzyme, wherein detection of the novel nucleic acid molecule indicates the presence of the contaminant in the sample.

For the detection methods referred to in this section, the features of the methods of the invention, set out in more general terms above, apply equally (and are not repeated for reasons of conciseness). Thus, any and all of the embodiments in which an enzyme reacts with a nucleic acid molecule to allow the nucleic acid molecule to be extended to generate a novel nucleic acid molecule are encompassed by this aspect of the invention.

In particular, the most preferred enzyme for use in the methods is a phosphatase. Any and all suitable phosphatases are contemplated within the scope of the invention (as discussed in more detail above).

The enzyme, which is preferably a phosphatase, may be linked to the reagent by any known manner. Suitable linking techniques are well known to those of skill in the art. In fact, phosphatase conjugated antibodies are routinely used in a whole range of immunoassays and these types of molecule are useful in the present methods.

As mentioned above, a preferred type of detection reaction which is utilised is one incorporating the polymerase embodiment which relies only on an amplification step due to the presence of dsDNA molecules which have 3' phosphate groups and single stranded sections. A preferred reaction scheme is set out in detail in FIGS. 7 and 8. Thus, the most preferred chemical moiety is a phosphate group.

In one embodiment the contaminant is a toxin. Preferably, the toxin is a mycotoxin, in particular an aflatoxin. Mycotoxins are toxic metabolites produced by certain fungi. These toxins can contaminate a number of food stuffs and thus present a danger to humans and animals alike. Aflatoxins are potent toxins produced as secondary metabolites by *Aspergillus* fungi, in particular by *Aspergillus flavus* and *Aspergillus parastitcus*. These toxins have been shown to have a number of deleterious effects, including carcinogenic, mutagenic and immunosuppressive activities. The major types of aflatoxin comprise aflatoxin B1, B2, G1 and G2. Additional aflatoxins include aflatoxins M1, M2, B2A and G2A.

The sample will generally be one suspected of, or which required testing for, the presence of the contaminant. Any type of sample may be used in which the contaminant may be present. Thus, by way of exemplification and not limitation, water supplies, pharmaceutical products, cosmetic products, beverages, clinical samples including blood and platelet samples and food samples may all be tested for the presence of the contaminant or contaminants of interest.

It is also possible to utilise any suitable clinical sample to test a subject of interest to determine if a contaminant has been consumed. The subject is most preferably a human subject, but may include an animal subject such as poultry and/or livestock. Specific examples include cattle, pigs, sheep, horses etc. Such a method is intended to be an in vitro method utilising an isolated sample. However, in one embodiment the method may additionally comprise the step of obtaining a suitable sample from the subject under test.

The reagent may be any reagent which is capable of specifically binding to the contaminant in question. In one preferred embodiment, the reagent comprises an antibody. However, it may include other suitable binding molecules to include lectins, receptors and nucleic acid based molecules. As mentioned above, the term "antibody" incorporates all derivatives and variants thereof which retain antigen binding capabilities. Both monoclonal and polyclonal antibodies may be utilised. Derivatised versions, which may be humanized versions of non-human antibodies for example, are also contemplated. Derivatives include, but are not limited to, heavy chain antibodies, single domain antibodies, nanobodies, Fab fragments, scFv etc.

In one preferred embodiment, the contaminant is effectively immobilised during the method. For example a suitable reagent capable of specifically binding to the contaminant may be bound to a solid phase (as are described above) in order to effectively immobilise the contaminant during the detection reaction. The nature of the reagent is discussed supra. The immobilised contaminant then acts to "capture" a second reagent specific for the contaminant. This second reagent is linked to an enzyme capable of adding or removing a chemical moiety to from a nucleic acid molecule, thereby conferring the nucleic acid molecule with the ability to be extended to generate a novel detectable nucleic acid molecule. Thus, the presence of the contaminant is linked directly to production of the novel nucleic acid molecule.

To detect a small molecule such as aflatoxin it may be necessary to employ a competitive immunoassay format. Competitive assays rely upon competition for (a limited number of) binding sites between labelled antigen and test sample antigen. A lower level of "label", being detected is indicative of higher levels of the test sample antigen. In the present invention, the antigen is labelled with a suitable enzyme which is capable of adding or removing a chemical moiety to or from a nucleic acid molecule, thereby conferring the nucleic acid molecule with the ability to be extended to generate a novel detectable nucleic acid molecule. This enzyme in conjunction with suitable nucleic acid molecules (as discussed above in more detail) can be used as a suitable detection system in a competitive assay format according to the invention. Suitable washing steps may be implemented accordingly in order to remove any unbound labelled antigen.

In the case of a toxin, such as aflatoxin, a specific reagent, such as an antibody, capable of binding the toxin is immobilised to a surface, such as a microplate for example. Free aflatoxin in the sample competes for the immobilised reagent, preferably antibody, binding sites with a conjugate consisting of alkaline phosphatase linked, for example by covalent linkage, to an aflatoxin moiety. Thus, in this embodiment, higher levels of the (aflatoxin) toxin in the sample leads to lower levels of the novel nucleic acid molecule being detected.

Thus, in one aspect the invention provides a method of detecting a contaminant in a sample comprising:
  a) applying the sample to a solid support upon which is immobilised a reagent capable of binding to the contaminant in the presence of the same contaminant linked to an enzyme which is capable of adding or removing a chemical moiety to or from a nucleic acid molecule, thereby conferring the nucleic acid molecule with the ability to be extended to generate a novel detectable nucleic acid molecule;
  b) incubating under conditions which permit enzyme activity; and
  c) determining the presence or level of the novel nucleic acid molecule, wherein an absence or low level of the novel nucleic acid molecule is indicative of a higher level of contaminant in the sample.

Thus, if more contaminant is present in the sample, reduced levels of the novel nucleic acid molecule will be detected. The conjugate is formed from the same contaminant type as the contaminant of interest so that a competitive assay may be employed.

For the avoidance of doubt, it is hereby stated that the steps of the various methods may be carried out at the same time (see above), and in a single tube (real time) format.

Diagnostic Methods for Detection of Non-Infectious Disease

Many phosphatases are known to have disease associations. For example elevated levels of prostatic acid phosphatase (PAP) are known to be linked to prostate cancer. By utilising suitable nucleic acid molecules, capable of being dephosphorylated by PAP, which thus confers on the nucleic acid molecule the ability to be extended to generate a novel nucleic acid molecule, a diagnostic test for prostate cancer may fall within the scope of the present invention.

Alkaline phosphatase is an important enzyme mainly derived from the liver and bones. It is found in lower amounts in the intestines, placenta, kidneys and leukocytes. Furthermore, alkaline phosphatase levels in serum have been shown to be increased in subjects suffering from a range of conditions. Maldonado et al.—Extremely high levels of alkaline phosphatase in hospitalized patients. *J Clin Gastroenterol.* 27(4): p 342-345 (December 1998), (incorporated herein by reference) have showed that serum alkaline phosphatase levels are markedly elevated in patients with sepsis, AIDS and malignancies. Wiwanitkit—High serum alkaline phosphatase levels, a study in 181 That adult hospitalized patients. *BMC Family Practice.* 2(1): 2 (July 2002) (incorporated herein by reference) found high serum alkaline phosphatase levels in patients with obstructive biliary diseases, infiltrative liver diseases, sepsis and cholangiocarcinoma. By sensitively detecting serum alkaline phosphatase using the method of the invention a diagnostic test may be envisaged for diagnosing each of these conditions, without the need for a large sample from the patient.

Thus, the invention provides a method of diagnosing prostate cancer in a mammalian subject comprising
allowing a sample obtained from the subject under test to be tested for the presence of prostatic acid phosphatase (PAP) to interact with a nucleic acid molecule; and
testing for interaction of PAP with the nucleic acid molecule by detecting a novel nucleic acid molecule produced by extension of the original nucleic acid molecule, whereby the presence of the novel nucleic acid molecule is indicative of the presence of prostatic acid phosphatase (PAP) in the sample and is taken as an indication that the subject may have or has prostate cancer.

Similarly the invention provides a method of diagnosing a disease associated with elevated serum alkaline phosphatase levels, including any one of sepsis, AIDS, malignancies, obstructive biliary diseases, infiltrative liver diseases, sepsis and cholangiocarcinoma in a mammalian subject comprising
allowing a sample obtained from the subject to be tested for the presence of serum alkaline phosphatase to interact with a nucleic acid molecule; and
testing for interaction of serum alkaline phosphatase with the nucleic acid molecule by detecting a novel nucleic acid molecule produced by extension of the original nucleic acid molecule, whereby the presence of the novel nucleic acid molecule is indicative of the presence of serum alkaline phosphatase in the sample and is taken as an indication that the subject has or may be susceptible to a disease associated with elevated serum alkaline phosphatase levels, which may be any one of sepsis, AIDS, malignancies, obstructive biliary diseases, infiltrative liver diseases, sepsis and cholangiocarcinoma for example.

In this context the "sample" will generally be a clinical sample. The sample being used will depend on the condition that is being tested for. In the case of diagnosing prostate cancer a suitable prostate sample from the patient may be required. Alternatively a blood sample may be utilised, since elevated PAP levels are found in the blood of a patient suffering from prostate cancer. Typical samples which may be used, but which are not intended to limit the invention, include whole blood, serum, plasma, urine etc. taken from a patient, most preferably a human patient.

In a most preferred embodiment the test will be an in vitro test carried out on a sample removed from a subject.

In a further embodiment the above-described diagnostic methods may additionally include the step of obtaining the sample from a subject. Methods of obtaining a suitable sample from a subject are well known in the art. Alternatively, the method may be carried out beginning with a sample that has already been isolated from the patient in a separate procedure. The diagnostic methods will most preferably be carried out on a sample from a human, but the method of the invention may have diagnostic utility for many animals.

The diagnostic methods of the invention may be used to complement any already available diagnostic techniques, potentially as a method of confirming an initial diagnosis. Alternatively, the methods may be used as a preliminary diagnosis method in their own right, since the methods provide a quick and convenient diagnostic method. Furthermore, due to their inherent sensitivity, the diagnostic methods of the invention will require only a minimal sample, thus preventing unnecessary invasive surgery.

For the avoidance of doubt, it is hereby stated that the preferred features of the method of the invention, as discussed in general terms above, apply equally to the diagnostic aspects of the invention (especially the ligation, blocking duplex and polymerase embodiments).

Kits

The invention also provides kits which may be used in order to carry out the methods of the invention. The kits may incorporate any of the preferred features mentioned in connection with the methods of the invention above.

Accordingly, in a further aspect of the invention there is provided a kit for detecting an enzyme capable of adding or removing a chemical moiety to or from a nucleic acid molecule, which thereby confers the nucleic acid molecule with the ability to be extended to generate a novel detectable nucleic acid molecule, comprising:
a nucleic acid molecule which is capable of being acted upon by the enzyme; and
means for detecting the novel nucleic acid molecule produced only if the enzyme is present.

In one embodiment, the novel nucleic acid molecule is produced by ligation or polymerisation, as discussed in detail above with respect to the methods of the invention. Thus, the preferred nucleic acid molecules described above are preferably included in the kits of the invention.

The kit may advantageously be used to complement already available kits which are based on using the target enzyme in question. Thus, for example, a standard ELISA kit will probably contain a suitable chromogenic or chemiluminescent substrate in order to detect if the enzyme, such as horseradish peroxidase or alkaline phosphatase has, in fact, bound via an antibody to the site where an antigen/analyte is present. This step of detecting enzyme activity may be replaced by the kit of the invention, which may advantageously add an extra amplification step to sensitise the detection of an analyte/antigen still further.

In a preferred embodiment the kit may be used to enhance the sensitivity of an immunoassay which includes alkaline phosphatase as the enzyme to detect binding of the antibody to the analyte/antigen, by utilising alkaline phosphatase's ability to remove terminal phosphates from DNA and RNA molecules. Thus in a preferred embodiment a kit is provided wherein the nucleic acid molecule has a 3' terminal phosphate group and additionally comprises a further nucleic acid molecule having a terminal 5' phosphate group. Such a kit may be used in the preferred "ligation" embodiments of the invention, described in detail above.

In a further embodiment, the kit further comprises a suitable ligase, which is capable of ligating the nucleic acid molecule to the further nucleic acid molecule provided the 3' terminal phosphate of the nucleic acid molecule has been cleaved by phosphatase activity. Preferably, the ligase is T4 DNA ligase or T4 RNA ligase and the nucleic acid molecules (including the further nucleic acid molecules) are ds or ss accordingly.

In an additional embodiment, the novel detectable nucleic acid molecule is produced by ligation of a nucleic acid molecule which is double stranded and has a 5' overhang to which is attached a 5' terminal phosphate group. Such a kit preferably additionally comprises a further ds nucleic acid molecule having a 5' overhang and a terminal 5' phosphate group attached to this.

The kit preferably further comprises a blocking ds nucleic acid molecule which is capable of ligating to the nucleic acid molecule if the 5' phosphate has not been removed from the 5' overhang by phosphatase activity. Such blocking nucleic acid molecules are described in further detail above.

This kit may also further comprise a ligase, which is preferably T4 DNA ligase.

In an alternative kit embodiment, the novel nucleic acid molecule is produced by polymerisation. Such a kit is useful in the "polymerisation" aspects of the methods of the invention, as discussed in greater detail above.

Thus, in a particularly preferred embodiment, the kit comprises a nucleic acid molecule which comprises a single stranded DNA molecule in which a terminal 3' phosphate is present and/or an overlapping single stranded DNA molecule which is blocked at the 3' end such that it cannot be extended.

In another "polymerisation" embodiment, the kit comprises nucleic acid molecules which comprise partially double stranded DNA in which terminal 3' phosphates are present. As mentioned above, these 3' phosphate groups act as blocks to extension of the nucleic acid molecule, unless and until they are removed by phosphatase activity present in the sample. Thus, the single stranded elements of the partially dsDNA allow priming of nucleic acid synthesis if the terminal 3' phosphates are removed by the phosphatase in the sample.

Preferably, the dsDNA comprises partially double-stranded DNA formed by a 3' overlap of the two single strands of DNA. In the kits of the invention, the two strands may be initially provided separately, or in pre-annealed form.

In a different embodiment, the nucleic acid molecule comprises dsDNA with a nick in each strand (as discussed in more detail supra). The nicks in the dsDNA expose one or more 3' phosphates at the location of the nicks, which can be acted upon by a phosphatase, if present in the test sample.

These kits may include suitable components and reagents required for amplification, as discussed in greater detail below.

In one further embodiment, the kit comprises a nucleic acid molecule which comprises dsDNA with one strand having a 5' overhang and wherein the shorter strand has a 3' terminal phosphate group attached. Preferably, this kit further comprises a polymerase and labelled nucleotides (dNTPs). The label may be a fluorescent label, radiolabel or mass label for example, as discussed in greater detail above. Thus, in use, the kit will allow detection of incorporation of the labelled nucleotides to produce a novel detectable nucleic acid molecule in the presence of phosphatase which removes the 3' phosphate from the nucleic acid molecule and thus allows the nucleic acid molecule to act as a primer to direct nucleic-acid synthesis utilising the overhang longer strand as a template.

In an alternative embodiment, the nucleic acid molecule comprises dsDNA with one strand having a 5' overhang and incorporating uracil nucleotides and wherein the shorter strand has a 3' terminal phosphate group attached.

Preferably, this kit further comprises a polymerase, Uracil N-glycosylase and nucleotides (dNTPs). These components should be provided in suitable form for use and may be accompanied by appropriate buffers. This applies to all components of the kits of the invention. The incorporation of uracil in the longer strand makes it susceptible to the action of UNG. Thus, once the complementary strand has been synthesised, the UNG can digest the originally longer strand. This leaves a ss novel detectable nucleic acid molecule which can be detected to determine the presence of the phosphatase in the sample. If phosphatase is not present in the sample, the 3' phosphate group will not be removed and extension of the nucleic acid molecule can not be catalysed by the polymerase.

Preferred polymerases for inclusion in the kits of the invention include Taq, Pfu and Vent. Preferably, the polymerases for inclusion in the kits of the invention and for use in the methods of the invention lack or have a deficiency in their 3'-5' exonuclease activity.

As mentioned above, the method of the invention will prove maximally sensitive when the novel nucleic acid molecule generated as a result of the addition or removal of a chemical moiety to the nucleic acid molecule and as catalysed by the modifying enzyme is detected using nucleic acid amplification techniques. As aforementioned preferred amplification techniques include PCR, Rolling circle replication, NASBA, 3SR and TMA techniques. In the case of nucleic acid amplification techniques, well known in the art, sequence specific primers are required to allow specific amplification of the product with minimal production of false positive results. To this end, the kits of the invention may preferably include appropriate sequence specific primers.

The kit may also include reagents necessary for a nucleic acid amplification step. Reagents may include, by way of example and not limitation, amplification enzymes, probes, positive control amplification templates, reaction buffers etc. For example, in the PCR method, possible reagents include a suitable polymerase such as Taq polymerase and appropriate PCR buffers, and in the TMA method the appropriate reagents include RNA polymerase and reverse transcriptase enzymes. All of these reagents are commercially available and well known in the art.

The kit may further include components required for real time detection of amplification products, such as fluorescent probes for example. As aforementioned the relevant real-time technologies, and the reagents required for such methods, are well known in the art and are commercially available. Suitable probes for use in these real-time methods may also be designed, in order that they may be used in conjunction with the nucleic acid molecules incorporated into the kits of the invention for their ability to be modified by appropriate enzyme activity. Thus, for example using the TAQMAN® technique, the probes may need to be of sequence such that they can bind between PCR primer sites on the novel nucleic acid molecule generated by the methods of the invention in the presence of the enzyme to be detected. Similarly, MOLECULAR BEACONS probes may be designed that bind to a relevant portion of the nucleic acid sequence incorporated into the kits of the invention. If using the SCORPION probe technique for real time detection the probe will need to be designed such that it hybridizes to its target only when the target site has been incorporated into the same molecule by extension of the tailed primer. For LIGHTCYCLER, two FRET probes are required which can bind to neighbouring binding sites on the novel nucleic acid molecule and thus generate a fluorescent signal. For the AMPLIFLUOUR system, the primers will need to be appropriately designed to contain a suitable hairpin, which is disturbed by binding of the primer to a site on the novel detectable nucleic acid molecule. The design of these primers and probes is a matter of routine for the skilled person and they may be designed to order. Any of these detection techniques, and others, may be incorporated into the kits of the invention. Suitable probes are accordingly included in a further aspect of the kits of the invention.

A kit for detection of a phosphatase associated with an infectious agent is also provided which, in addition to any of the components above may additionally comprise a specific reagent such as an antibody selective for an infectious agent-specific phosphatase. Thus, for example, the kit may also contain;
- a nucleic acid molecule which is capable of being acted upon by the phosphatase associated with an infectious agent in order to allow that nucleic acid molecule to be extended (in a downstream process) in order to generate a novel detectable nucleic acid molecule; and
- means for detecting the novel detectable nucleic acid molecule.

In one embodiment the infectious agent is *Aspergillus* or *Staphyloccocus* species.

A kit for detection of a contaminant in a sample is also provided which, in addition to any of the components above may additionally comprise a reagent capable of specifically binding to the contaminant, wherein the reagent is linked to an enzyme which is capable of adding or removing a chemical moiety to or from a nucleic acid molecule, thereby conferring the nucleic acid molecule with the ability to be extended to generate a novel detectable nucleic acid molecule.

The enzyme is preferably a phosphatase, as discussed in greater detail above.

The contaminant is preferably a toxin, as discussed supra. In one embodiment, the toxin is a mycotoxin, in particular an aflatoxin. In a further embodiment, the aflatoxin comprises, consists essentially of or consists of any of aflatoxin B1 and/or B2 and/or G1 and/or G2 and/or M1 and/or M2 and/or B2A and/or G2A.

In a preferred kit of the invention, the reagent comprises an antibody or a derivative thereof that retains the ability to specifically bind to the contaminant.

The kits may also preferably contain means for immobilising the contaminant. Any type of solid support may be utilised, to include beads, plates, columns etc. as would be well known to the skilled person. A suitable contaminant binding reagent may be provided immoblised on the solid support.

For a competitive immunoassay kit, the kit may further comprise a contaminant, such as aflatoxin, which is linked, for example by covalent linkage, to a suitable enzyme, preferably phosphatase. The presence of the contaminant in a sample is detected by determining the decrease in the novel nucleic acid molecule produced as a result of the contaminant competing for binding sites. The description of the method of the invention provided above is applicable here.

The kit may also comprise a suitable contaminant binding reagent, such as an antibody immoblised on a solid support (as discussed above).

EXPERIMENTAL SECTION

The invention will be further understood with reference to the following examples, together with the accompanying tables and figures in which.

Figure 7:
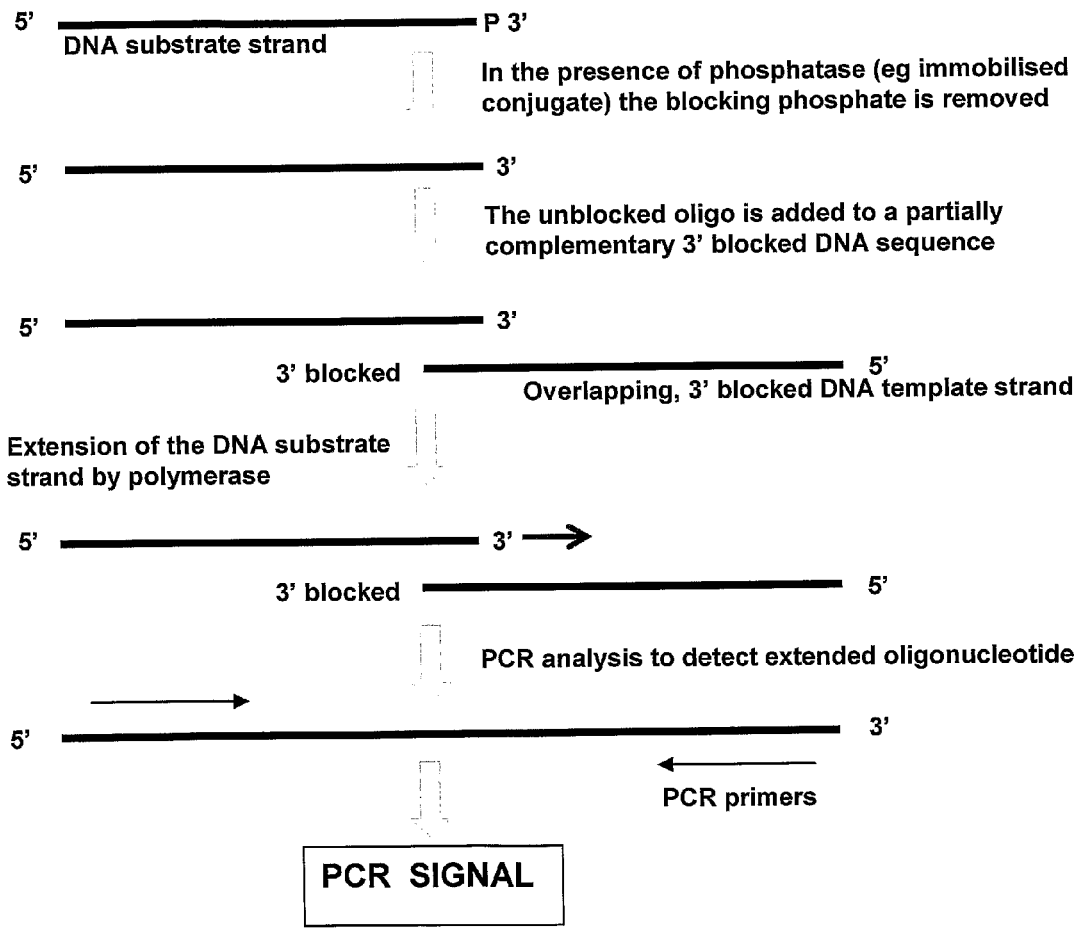

FIG. 7 shows schematically a most preferred "polymerisation" embodiment of the invention in general terms. Whilst PCR is shown as the amplification process utilised, this is not intended to be limiting with respect to the invention. Any suitable nucleic acid amplification technique may be utilised.

Figure 8:
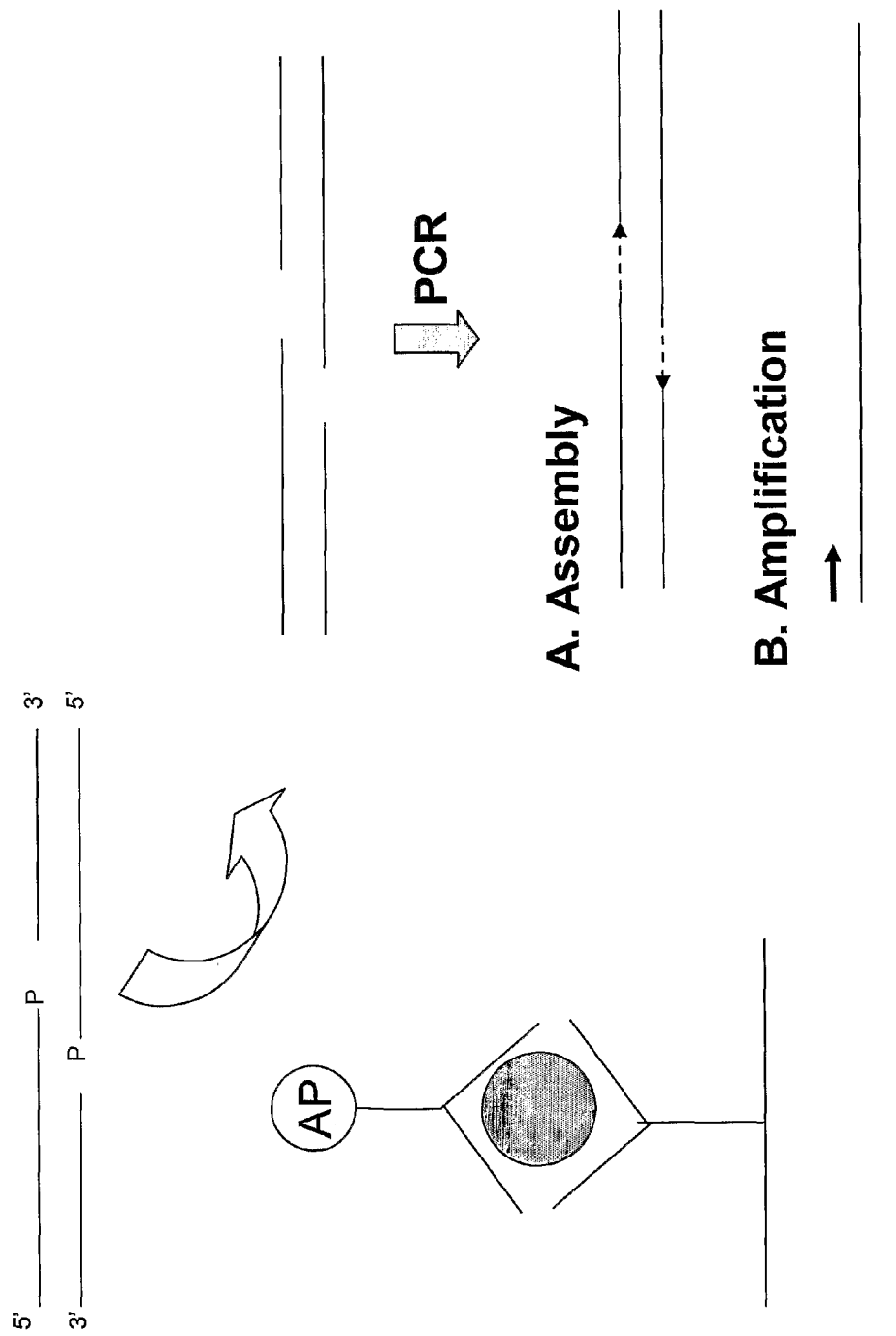

FIG. 8 represents a schematic of a polymerase based approach which involves use of nicked dsDNA which incorporates 3' (terminal) phosphates.

Figure 9:
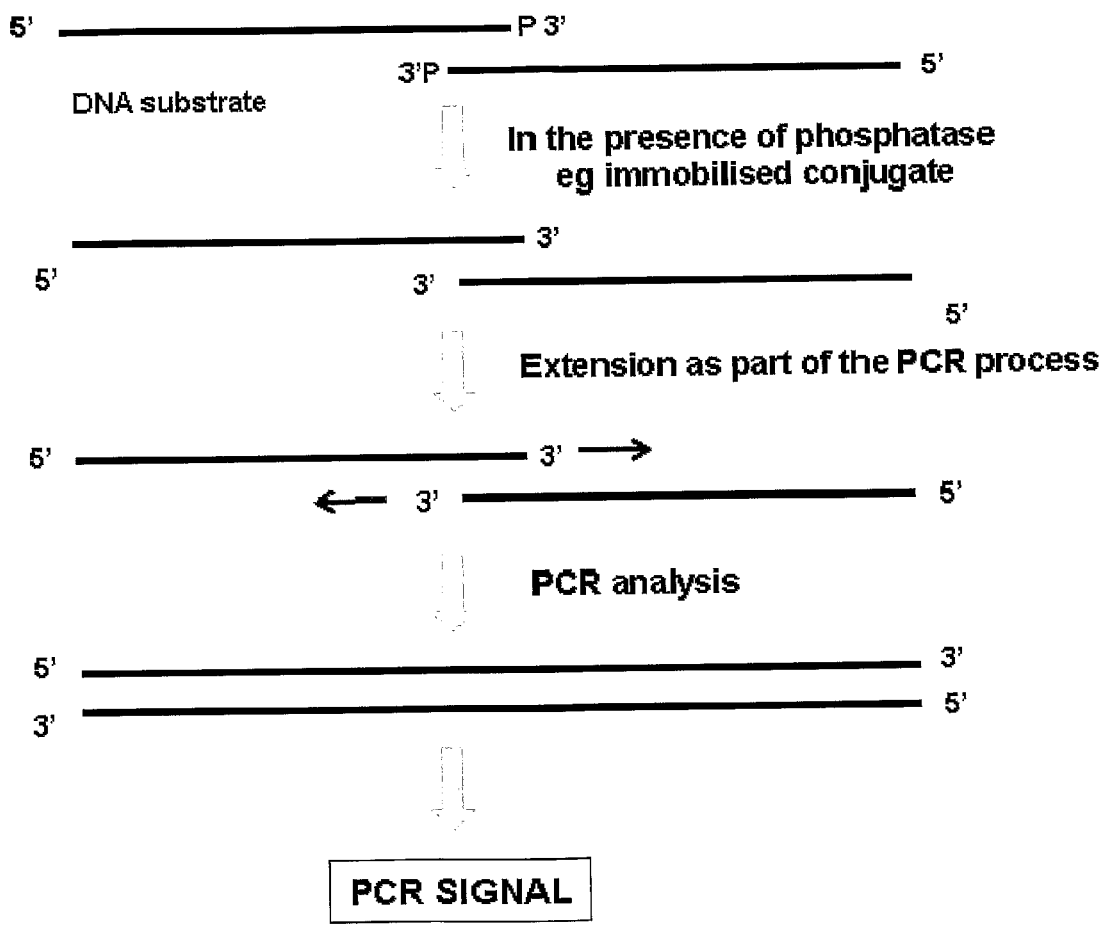

FIG. 9 represents a schematic diagram of a similar polymerase based approach to that shown in FIG. 7. Here, however, partially double-stranded DNA is utilised which incorporates strands having 3' terminal phosphate groups attached. Suitable dsDNA molecule may be formed by, for example, the annealing of two 3' phosphate blocked oligonucleotides. The 3' phosphate blocked oligonucleotides may be pre-annealed or may be utilised in the methods of the invention individually, with annealing occurring for example following an initial incubation period.

Figure 10:
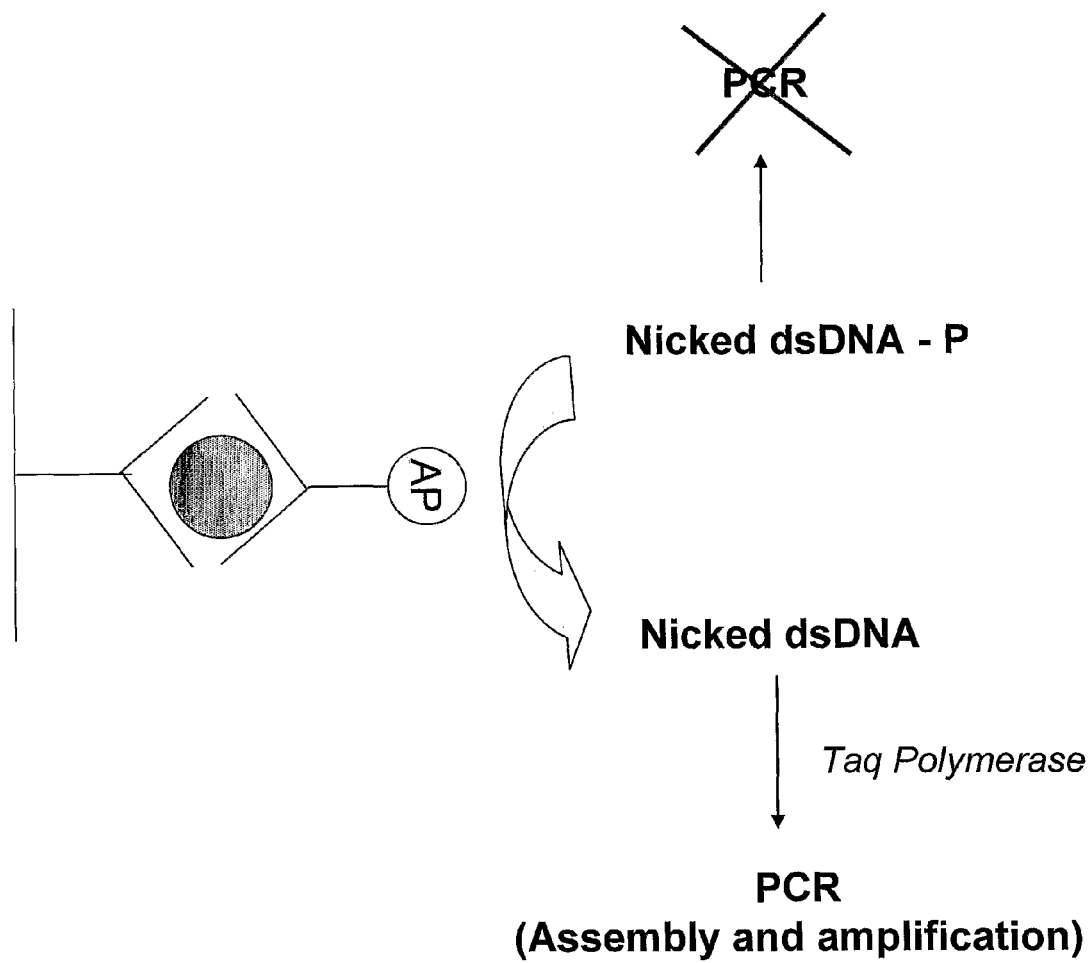

FIG. 10 shows schematically how the methods of the invention may be utilised in order to detect a contaminant (grey circle) in a sample. The binding reagents are represented appropriately, including one component which is immobilised. Alkaline phosphatase is represented by a labelled (AP) filled in circle. The top part of the figure shows the situation if no contaminant is present, and the lower part of the figure shows the detection technique utilised if a contaminant is present in the sample.

Figure 11:
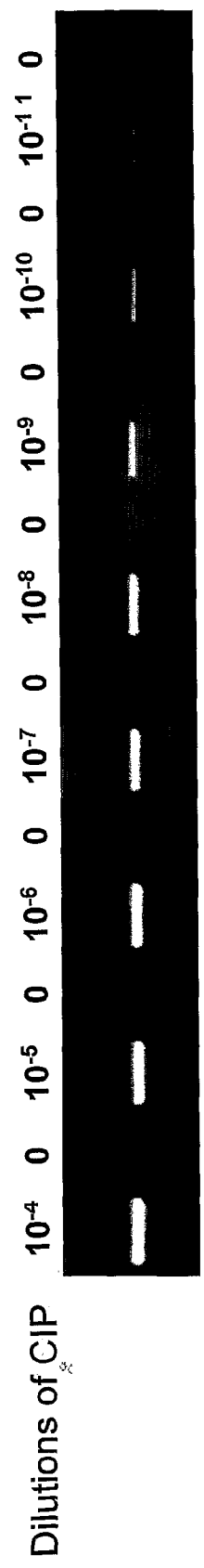

FIG. 11 shows the sensitivity of the methods described herein and represented schematically in FIG. 8.

EXAMPLE 1

Detection of Streptavidin Alkaline Phosphatase Conjugate Using an Immobilised Phosphorylated Duplex and a Blocking Duplex Approach Introduction A streptavidin alkaline phosphatase (S-AP) conjugate was used as a model system to investigate the detection of alkaline phosphatase (AP) using a phosphorylated nucleic acid substrate. In this example the duplex DNA is bound directly or indirectly through the antigen and is thus is brought into close proximity to an AP conjugate which is similarly bound. The AP removes the 5' phosphate from the proximate duplex which prevents it ligating in a subsequent step to a complimentary blocking duplex (ligation does not occur because neither duplexes have a 5' phosphate necessary for ligation).

If the original duplex DNA is not bound to the antigen and/or is not proximate to an AP the 5' phosphate is not removed and ligation with the blocking duplex can now occur. Once ligated this prevents any further ligation steps. However, any bound duplex which has been protected from the blocking duplex by dephosphorylation is now susceptible to ligation by the detection duplex which has a phosphorylated 5' complementary single strand overhang. A new ligated molecule is thus formed which can be detected by PCR (or other nucleic amplification technique) across the ligated junction.

Method
1. The S-AP conjugate (1 mg/ml stock in TBS) was serially diluted in TBS and 100 µl used to coat a maxisorp plastic microtiter well for 60 min at room temperature.
2. After washing ×5 with TBS 0.5% Tween20, 100 µl duplex oligo ½ was added in TBS 0.5% Tween 20 [duplex oligo ½ with a biotin at one end and a EcoRI cleavable site at the other end was prepared by heating oligo 1 (5' Biotin GCC GAT ATC GGA CAA CGC CGA ACT GCG AAG GGC GAA TTC CTC GTC—SEQ ID NO:1) with oligo 2 (5' GAC GAG GAA TTC GCC CTT CGC AGT TCG GCG TTG TCC GAT ATC GGC—SEQ ID NO:2) both at 50 pmol/µl in TBS to 90° C. for 5 min followed by slow cooling to room temperature]. Two concentrations of oligo ½ were used; 0.5 pmoles (reaction condition A) and 5 pmoles (reaction condition B) per well.
3. After 60 min the wells were washed ×3 in TBS 0.5% Tween20 and 100 µl of EcoRI mix added containing 1× EcoRI buffer and 10 units of EcoRI enzyme (New England Biolabs). This exposes the cut end of the molecule which has a 5' single strand phosphate end which is complementary to both the blocking and the detection duplexes.
4. After incubation at 37° C. for 30 min the wells were washed ×3 in TBS 0.5% Tween20 and 100 µl of blocking duplex oligo ¾ added [duplex oligo ¾ with a complementary 5' overhang to the cut oligo ½ duplex was prepared by heating oligo 3 (5' AAT TAC GAC CAC ATC AAC C—SEQ ID NO:3) with oligo 4 (5'CCG GTT GAT GTG GTC GT—SEQ ID NO:4) both at 50 pmol/µl in TBS to 90° C. for 5 min followed by slow cooling to room temperature] at 1 nmol/ml in 1× ligase buffer containing 400 units/ml T4 DNA ligase (New England Biolabs).
5. After 60 min at room temperature wells were washed ×3 with TBS 0.5% Tween20 and 50 µl of detection duplex oligo ⅚ added [duplex oligo ⅚ with a complementary 5' phosphate-containing overhang to the cut oligo ½ duplex was prepared by heating oligo 5 (5' AAT TGG TCA TCA GCC GCG TGG CCT TTG TCA CCG ACG CCT A—SEQ ID NO:5) with oligo 6 (5' phosphate CCT AGG CGT CGG TGA CAA AGG CCA CGC GGC TGA TGA CC—SEQ ID NO:6) both at 50 pmol/µl in TBS to 90° C. for 5 min followed by slow cooling to room temperature] at 1 nmol/ml in 1× ligase buffer containing 400 units/ml T4 DNA ligase (New England Biolabs).
6. After 60 min at room temperature the wells were washed ×4 in TBS 0.5% Tween20 and 50 µl of standard PCR mix added (New England Biolabs) containing Taq DNA polymerase and primers 5' GGA CAA CGC CGA ACT GCG AAG GGC (SEQ ID NO:7) and 5' TAG GCG TCG GTG ACA AAG GCC ACG (SEQ ID NO:8). This was overlayed with 50 µl of mineral oil and heated on a flat heating block at 92° C. for 7 min.
7. The liquid was removed and PCR performed under the following conditions: 93° C. for 30 sec, 80° C. for 30 secs, 65° C. for 30 sec and 72° C. for 10 sec.
8. Aliquots of the PCR were removed at 25 and 30 cycles for analysis by electrophoresis on a 3% MetaPhor agarose gel.

Figure 1:
FIG. 1 shows detection of streptavidin alkaline phosphatase conjugate using an immobilised phosphorylated duplex and a blocking duplex approach.
Figure 1:

Results and Discussion (see FIG. 1)

Conditions B worked the best using the higher concentration of oligo ½. The $10^{-7}$ dilution could easily be differentiated from the control well. This represents 10 pg of S-AP of which perhaps only 1-2% is coated onto the plastic. This indicates that 100-200 fg of S-AP could be detected which, if extrapolating from this model system would suggest that the assay could have the potential to detect fg quantities of immobilised antigen.

EXAMPLE 2

Improved Detection of Streptavidin Alkaline Phosphatase Conjugate Using an Immobilised Phosphorylated Duplex and a Blocking Duplex Approach Introduction A streptavidin alkaline phosphatase (S-AP) conjugate was used as a model system to investigate the detection of AP alkaline phosphatase using a phosphorylated nucleic acid substrate. In this example the single-stranded overhang of the bound duplex was designed so that it was not palindromic thus avoiding duplex-duplex ligation of the same molecular species eg self ligation of the bound oligo ½ or the detection oligo ¾ that may have occurred in example 1.

Method
1. The S-AP conjugate (1 mg/ml stock in TBS) was serially diluted in TBS and 100 µl used to coat a maxisorp plastic microtiter well for 60 min at room temperature.
2. After washing ×5 with TBS 0.5% Tween20, 100 µl duplex oligo ½ at 50 pmoles/ml was added in TBS 0.5% Tween 20 [duplex oligo ½ with a biotin at one end and a Sty1 cleavable site at the other end was prepared by heating oligo 1 (5' Biotin GCC GAT ATC GGA CAA CGC CGA ACT GCG AAG GGC GAA GGC TCG TC—SEQ ID NO:9) with oligo 2 (5' GAC GAG CCT TGG CCC TTC GCA GTT CGG CGT TGT CCG ATA TCG GC—SEQ ID NO:10) both at 50 pmol/µl in TBS to 90° C. for 5 min followed by slow cooling to room temperature].
3. After 60 min the wells were washed ×3 in TBS 0.5% Tween20 and 50 µl of Sty1 mix added containing 1× Sty1 buffer and 2.5 units of Sty1 enzyme (New England Biolabs).
4. After incubation at 37° C. for 30 min the wells were washed ×3 in TBS 0.5% Tween20 and 100 µl of duplex oligo ¾ added [duplex oligo ¾ with a complementary 5' overhang to the cut oligo ½ duplex was prepared by heating oligo 3 (5'CAA GAC GAC CAC ATC AAC C—SEQ ID NO:11) with oligo 4 (5' CCG GTT GAT GTG GTC GT—SEQ ID NO:12) both at 50 pmol/µl in TBS to 90° C. for 5 min followed by slow cooling to room temperature] at 1 nmol/ml in 1× ligase buffer containing 400 units/ml T4 DNA ligase (New England Biolabs).
5. After 60 min at room temperature wells were washed ×3 with TBS 0.5% Tween20 and 50 µl of duplex oligo ⅚ added [duplex oligo ⅚ with a complementary 5' phosphate-containing overhang to the cut oligo ½ duplex was prepared by heating oligo 5 (5'CAA GCG TCA TCA GCC GCG TGG CCT TTG TCA CCG ACG CCT A—SEQ ID NO:13) with oligo 6 (5' phosphate CCT AGG CGT CGG TGA CAA AGG CCA CGC GGC TGA TGA CG—SEQ ID NO:14) both at 50 pmol/µl in TBS to 90° C. for 5 min followed by slow cooling to room temperature] at 1 nmol/ml in 1× ligase buffer containing 400 units/ml T4 DNA ligase (New England Biolabs).
6. After 60 min at room temperature the wells were washed ×4 in TBS 0.5% Tween20 and 50 µl of standard PCR mix added (New England Biolabs) containing Taq DNA polymerase and primers 5' GGA CAA CGC CGA ACT GCG AAG GGC (SEQ ID NO:7) and 5' TAG GCG TCG GTG ACA AAG GCC ACG (SEQ ID NO:8). This was overlayed with 50 µl of mineral oil and heated on a flat heating block at 92° C. for 7 min.
7. The liquid was removed and PCR performed under the following conditions: 93° C. for 30 sec, 65° C. for 30 sec and 72° C. for 10 sec.
8. Aliquots of the PCR were removed at 30 cycles for analysis by electrophoresis on a 3% MetaPhor agarose gel. Similarly coated dilutions of S-AP were washed and tested using the AMPAQ alkaline phosphatase amplified calorimetric substrate (DAKO).

Figure 2:
FIG. 2 shows improved detection of streptavidin alkaline phosphatase conjugate using an immobilised phosphorylated duplex and a blocking duplex approach.

Results and Discussion (see FIG. 2)

The $10^{-8}$ dilution could easily be differentiated from the control well. This represents 1 pg of S-AP of which perhaps only 1-2% is coated onto the plastic. This indicates that 10-20 fg of S-AP could be detected which, if extrapolating from this model system would suggest that the assay could have the potential to detect fg quantities of immobilised antigen. The amplified AMPAQ substrate (a sensitive calorimetric alkaline phosphatase substrate manufactured by Dako, UK) could only detect the $10^{-5}$ dilution of the S-AP but the I2PCR approach could detect a $10^{-8}$ dilution; which was 1000-fold more sensitive than using an AMPAQ substrate. The use of duplexes with non-palindromic single-stranded overhangs clearly enables a higher sensitivity to be achieved.

EXAMPLE 3

Figure 3:
FIG. 3 shows detection of streptavidin alkaline phosphatase conjugate using an immobilised duplex with a 3' phosphate—the ligation approach.
Figure 4:
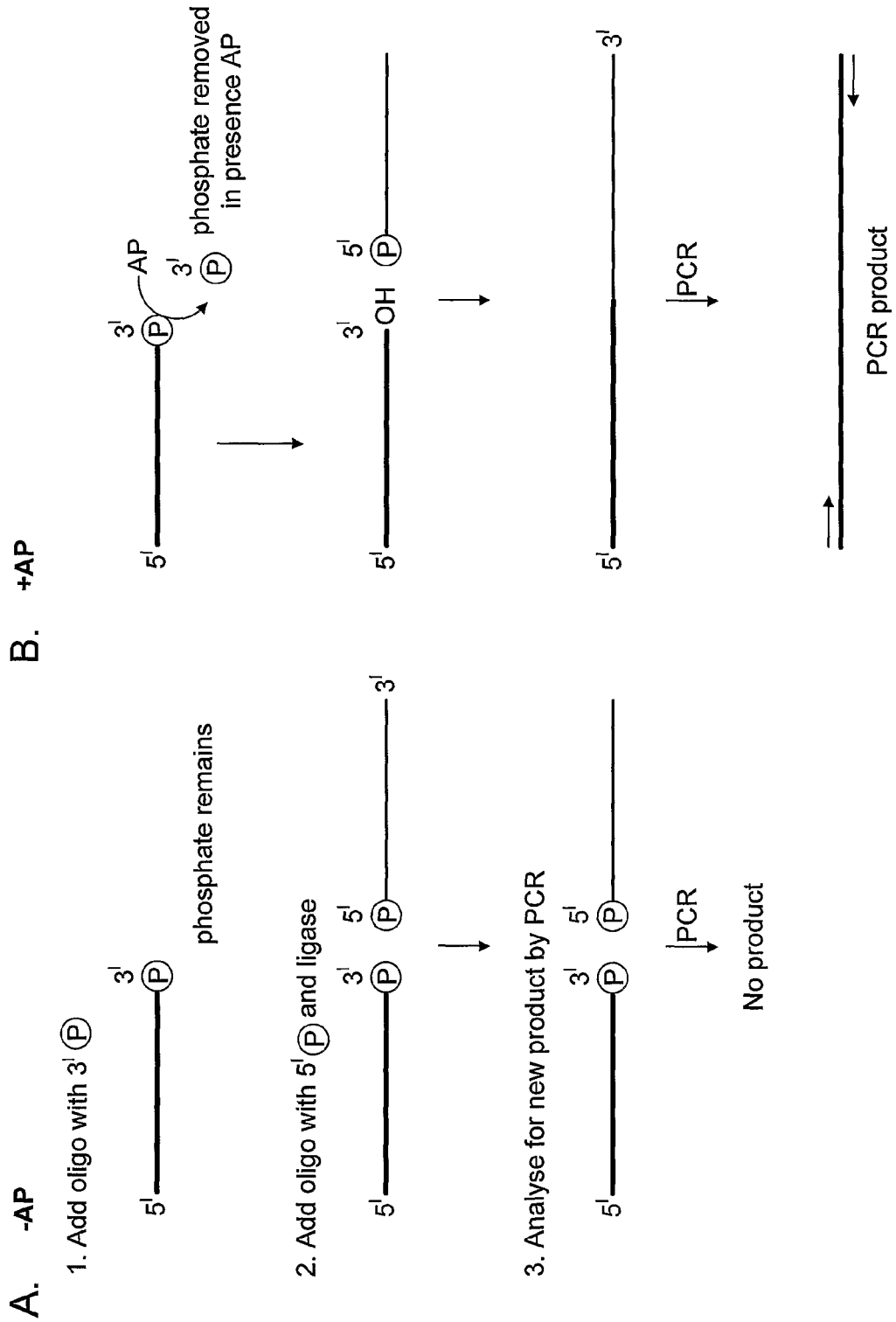
FIG. 4 shows schematically the ligation approach.
Figure 5:
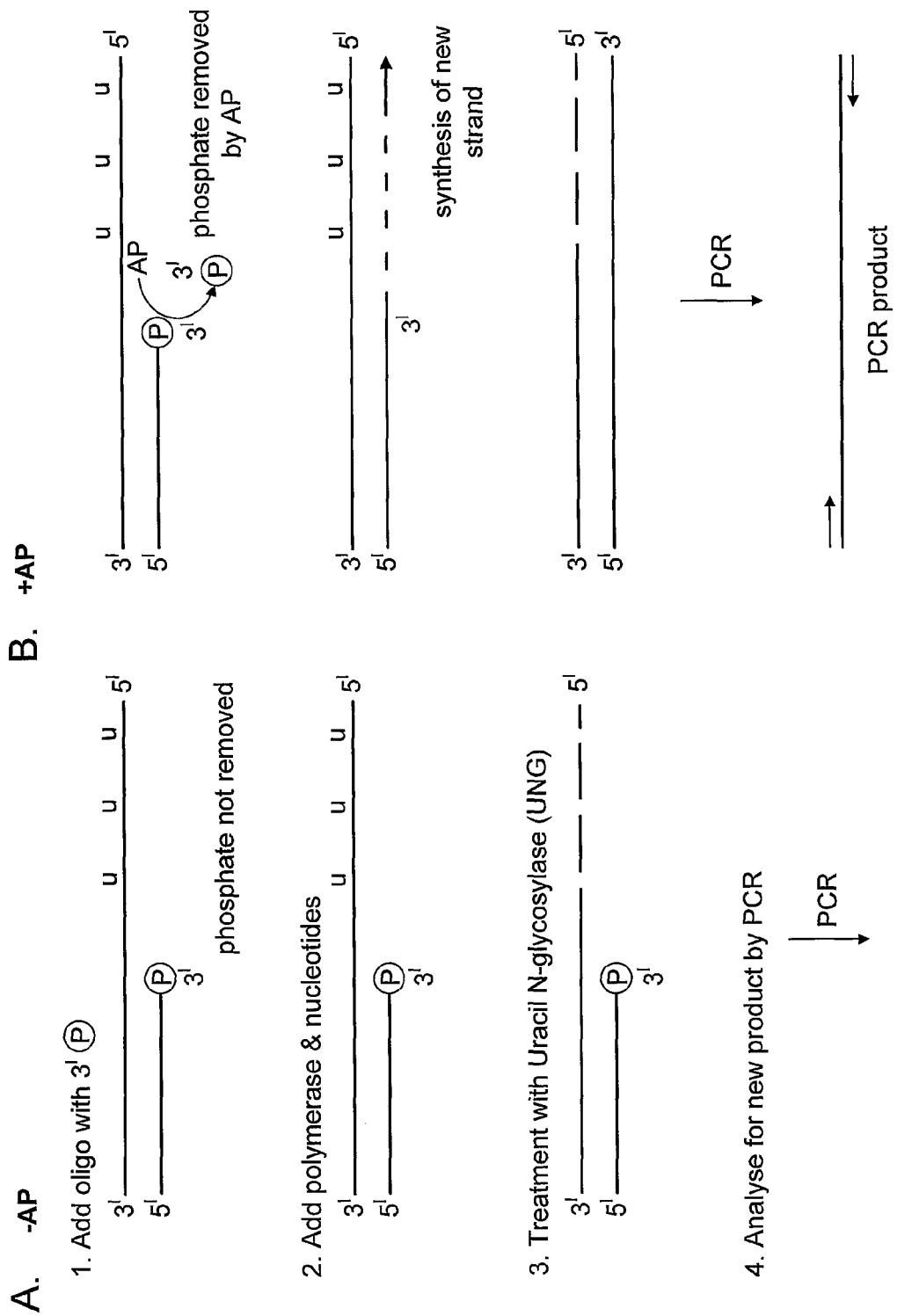
FIG. 5 shows schematically one of the polymerisation approaches.
Figure 6:
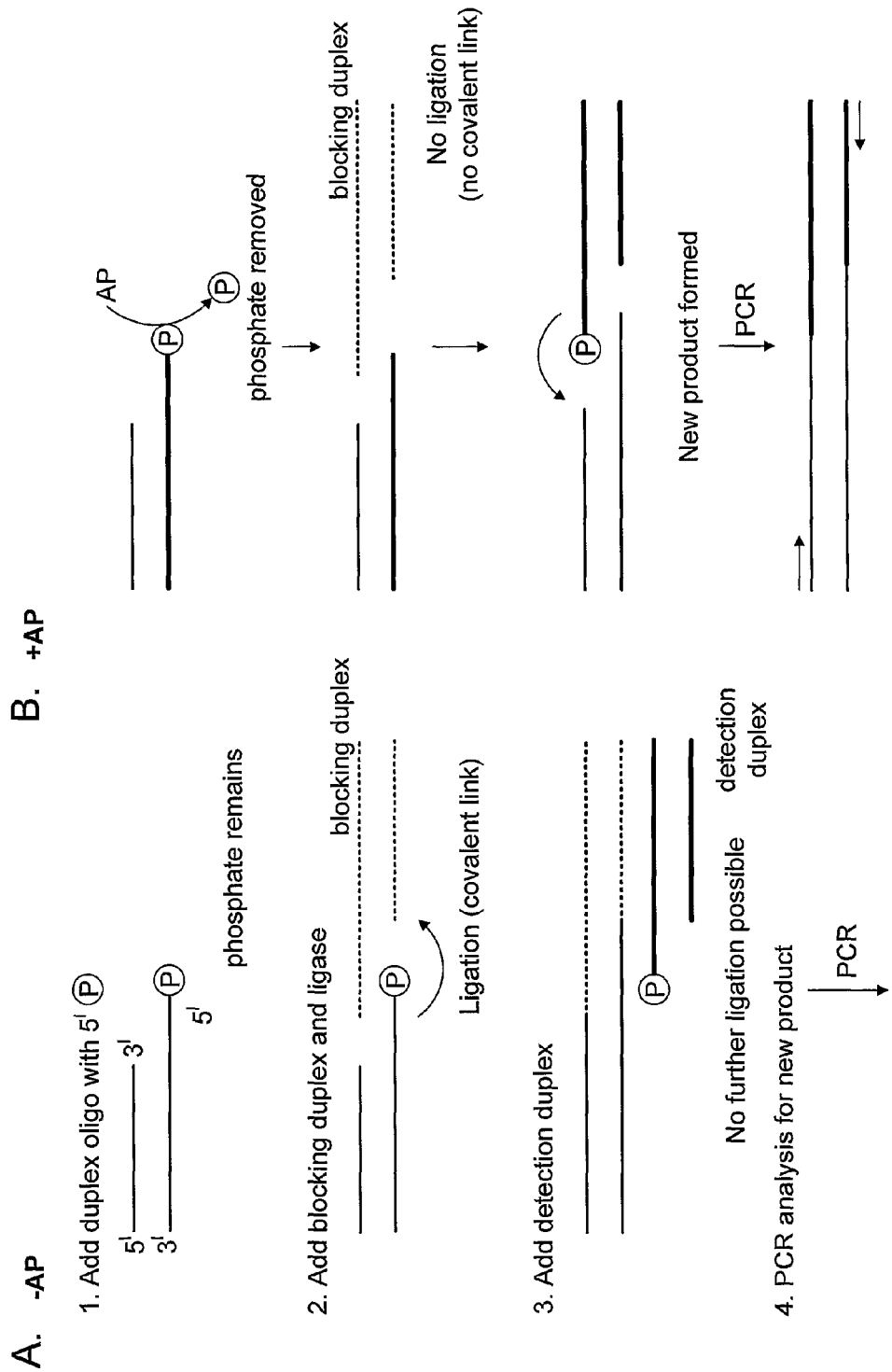
FIG. 6 shows schematically the blocking nucleic acid molecule (duplex) approach.

See FIG. 3

Detection of Streptavidin Alkaline Phosphatase Conjugate Using an Immobilised Duplex with a 3' Phosphate—the Ligation Approach Introduction A streptavidin alkaline phosphatase (S-AP) conjugate was used as a model system to investigate the detection of AP using a 3' phosphorylated nucleic acid substrate. In this example the single-stranded overhang for ligation was designed so that it cannot be ligated because of a blocking 3' phosphate moleclule (ligation requires the presence of a 3' exposed hydroxyl (OH) group and a 5' phosphate group). In this example the duplex DNA is bound directly or indirectly through the antigen and is thus is brought into close proximity to an AP conjugate which is similarly bound. The AP removes the 3' phosphate from the proximate duplex which then makes the duplex accessible for ligation to the detection duplex which has a phosphorylated 5' complementary single strand overhang. A new ligated molecule is thus formed which can be detected by PCR (or other nucleic amplification technique) across the ligated junction.

If the original duplex DNA is not bound to the antigen and/or is not proximate to an AP the 3' phosphate is not removed and ligation with the detection duplex cannot occur and no PCR product is generated. This method gives a more specific and sensitive detection than previous approaches outlined in examples 1 and 2 because it does not rely on blocking, which is likely to be less than 100% effective, but rather this approach is an activation process i.e. the bound duplex is rendered susceptible to ligation by the interaction of the AP.

Method

1. The S-AP conjugate (1 mg/ml stock in TBS) was serially diluted in TBS and 100 µl used to coat a maxisorp plastic microtiter well for 60 min at room temperature.
2. After washing ×5 with TBS 0.5% Tween20 100 µl duplex oligo ½ at 50 pmoles/ml was added in PBS 0.5% Tween20, 0.1 mM sodium vanadate (these conditions inhibit the activity of AP in this binding step) [duplex oligo ½ with a 3' biotin at one end and a 3' phosphate at the other end was prepared by heating oligo 1 (5' GCC GAT ATC GGA CAA CGC CGA ACT GCG AAG GGC CAA GGC TCG 3' phosphate—SEQ ID NO:15) with oligo 2 (5' CCT TGG CCC TTC GCA GTT CGG CGT TGT CCG ATA TCG GC 3' Biotin—SEQ ID NO:16) both at 50 pmol/µl in TBS to 90° C. for 5 min followed by slow cooling to room temperature].
3. After 30 min the wells were washed ×3 in TBS 0.5% Tween20 and 50 µl of detection duplex oligo ⅚ added [duplex oligo ⅚ with a complementary 5' phosphate single stranded overhang to the bound oligo duplex ½ was prepared by heating oligo 5 (5' GGT CAT CAG CCG CGT GGC CTT TGT CAC CGA CGC CTA—SEQ ID NO:17) with oligo 6 (5' phosphate TAG GCG TCG GTG ACA AAG GCC ACG CGG CTG ATG ACG—SEQ ID NO:18) both at 50 pmol/µl in TBS to 90° C. for 5 min followed by slow cooling to room temperature] at 1 nmol/ml in 1× ligase buffer containing 400 units/ml T4 DNA ligase (New England Biolabs).
4. After 60 min at room temperature the wells were washed ×4 in TBS 0.5% Tween20 and 50 µl of standard PCR mix added (New England Biolabs) containing Taq DNA polymerase and primers 5' GGA CAA CGC CGA ACT GCG AAG GGC (SEQ ID NO:7) and 5' TAG GCG TCG GTG ACA AAG GCC ACG (SEQ ID NO:8). This was overlayed with 50 µl of mineral oil and heated on a flat heating block at 92° C. for 7 min.
5. The liquid was removed and PCR performed under the following conditions: 93° C. for 30 sec, 65° C. for 30 sec and 72° C. for 10 sec.
6. Aliquots of the PCR were removed at 25 cycles for analysis by electrophoresis on a 3% MetaPhor agarose gel.

Results and Discussion (see FIG. 3)

The $10^{-11}$ dilution could easily be differentiated from the control no-S-AP well. This represents 1 fg of S-AP of which perhaps only 1-2% is coated onto the plastic. This indicates that $10^{-20}$ ag of S-AP could be detected which, if extrapolating from this model system would suggest that the assay could have the potential to detect attogram quantities of immobilised antigen.

EXAMPLE 4

Detection of Antigens in an ELISA Format Using an Immobilised Phosphorylated Duplex—the Blocking Duplex Approach Introduction This example demonstrates how the invention can be applied in an ELISA format for the detection of antigens such as *Chlamydia* antigens.

Method

1. Maxisorp microtiter plates (Nunc) were coated for 60 min with 100 µl anti-chlamydia LPS antibodies at 0.1-100 ng/ml in TBS (anti-chlamydia antibodies are widely available and are empirically investigated to find a pair that work together in an ELISA format).
2. Wells were washed ×3 with PBS and incubated with 100 µl 1.0-0.01 mg/ml biotinylation reagent (biotin amidocaproic acid 3-sulfo N-hydroxy succinimide ester, Sigma B1022) in PBS for 30 min.
3. Wells were washed ×3 with TBS then incubated with 100 ng/ml streptavidin in TBS 0.5% Tween20 for 60 min.
4. Wells were then washed ×5 with TBS Tween20. The capture plates were thus prepared and could be stored for weeks or months, dried, at 4° C. or could be used immediately.
5. Serial dilution of chlamydia LPS antigen were made in TBS 0.5% Tween20 and 100 µl of each dilution added to a coated well. Urinary tract swabs can be extracted using standard techniques into similar buffer and tested in a similar way.
6. After 60 min the wells were washed ×3 with TBS Tween20 and 1-10 ng of anti-chlamydia LPS AP conjugate (made following standard procedures) added in 100 µl TBS Tween20 containing duplex oligo ½ at 50 pmoles/ml [duplex oligo ½ with a biotin at one end and a Sty1 cleavable site at the other end was prepared by heating oligo 1 (5' Biotin GCC GAT ATC GGA CAA CGC CGA ACT GCG AAG GGC GAA GGC TCG TC—SEQ ID NO:9) with oligo 2 (5' GAC GAG CCT TGG CCC TTC GCA GTT CGG CGT TGT CCG ATA TCG GC—SEQ ID NO:10) both at 50 pmol/µl in TBS to 90° C. for 5 min followed by slow cooling to room temperature].
7. After 60 min the wells were washed ×3 in TBS 0.5% Tween20 and 50 µl of Sty1 mix added containing 1× Sty1 buffer and 2.5 units of Sty1 enzyme (New England Biolabs).
8. After incubation at 37° C. for 30 min the wells were washed ×3 in TBS 0.5% Tween20 and 100 µl of duplex oligo ¾ added [duplex oligo ¾ with a complementary 5' overhang to the cut oligo ½ duplex was prepared by heating oligo 3 (5' CAA GAC GAC CAC ATC AAC C—SEQ ID NO:11) with oligo 4 (5' CCG GTT GAT GTG GTC GT—SEQ ID NO:4) both at 50 pmol/µl in TBS to 90° C. for 5 min followed by slow cooling to room temperature] at 1 nmol/ml in 1× ligase buffer containing 400 units/ml T4 DNA ligase (New England Biolabs).
9. After 60 min at room temperature wells were washed ×3 with TBS 0.5% Tween20 and 50 µl of duplex oligo ⅚ added [duplex oligo ⅚ with a complementary 5' phosphate-containing overhang to the cut oligo ½ duplex was prepared by heating oligo 5 (5' CAA GCG TCA TCA GCC GCG TGG CCT TTG TCA CCG ACG CCT A—SEQ ID NO:13) with oligo 6 (5' phosphate CCT AGG CGT CGG TGA CAA AGG CCA CGC GGC TGA TGA CG—SEQ ID NO:14) both at 50 pmol/µl in TBS to 90° C. for 5 min followed by slow cooling to room temperature] at 1 nmol/ml in 1× ligase buffer containing 400 units/ml T4 DNA ligase (New England Biolabs).
10. After 60 min at room temperature the wells were washed ×4 in TBS 0.5% Tween20 and 50 µl of standard PCR mix added (New England Biolabs) containing Taq DNA polymerase and primers 5' GGA CAA CGC CGA ACT GCG AAG GGC (SEQ ID NO:7) and 5' TAG GCG TCG GTG ACA AAG GCC ACG (SEQ ID NO:8). This was overlayed with 50 µl of mineral oil and heated on a flat heating block at 92° C. for 7 min.
11. The liquid was then removed and PCR performed under the following conditions: 93° C. for 30 sec, 65° C. for 30 sec and 72° C. for 10 sec.
12. Aliquots of the PCR were removed at 30 cycles for analysis by electrophoresis on a 3% MetaPhor agarose gel.

EXAMPLE 5

Detection of Antigens in an ELISA Format Using an Immobilised Duplex with a 3' Phosphate—the Extension Approach Introduction This example demonstrates how the invention can be applied in an ELISA format for the detection of antigens such as *Chlamydia* antigens.

Method
1. Maxisorp microtiter plates (Nunc) were coated for 60 min with 100 µl anti-chlamydia LPS antibodies at 0.1-100 ng/ml in TBS (anti-chlamydia antibodies are widely available and are empirically investigated to find a pair that work together in an ELISA format).
2. Wells were washed ×3 with PBS and incubated with 100 µl 1.0-0.01 mg/ml biotinylation reagent (biotin amidocaproic acid 3-sulfo N-hydroxy succinimide ester, Sigma B1022) in PBS for 30 min.
3. Wells were washed ×3 with TBS then incubated with 100 ng/ml streptavidin in TBS 0.50 Tween20 for 60 min.
4. Wells were then washed ×5 with TBS Tween20.
5. Serial dilution of chlamydia LPS antigen were made in TBS 0.5% Tween20 and 100 µl of each dilution added to a coated well. Urinary tract swabs can be extracted using standard techniques into similar buffer and tested in a similar way.
6. After 60 min the wells were washed ×3 with TBS Tween20 and 1-10 ng of anti-chlamydia LPS AP conjugate (made following standard procedures) added in PBS Tween20, 1 mM sodium vanadate containing 10 ng DNA duplex (10 pmoles/ml oligo 1; 5' Biotin CCA GGC GAA AGG GGG ATG TGC TGC AA 3' (SEQ ID NO:19) phosphate annealed to long of a denatured template DNA [made by PCR of pUC19 with oligo 1 and oligo 3 (5' TCA CTC GCG TTG CGT TAA TTA CAC TC—SEQ ID NO:20) in a reaction mix in which the normal nucleotide dTTP is replaced by dUTP and then the product purified by affinity chromatography following standard methods].
7. After 60 min the wells were washed ×5 in TBS tween20 and 50 µl of a standard PCR mix added containing normal concentrations of dNTPs, Taq polymerase, 1×PCR buffer, and 1 unit UNG-glycosylase and incubated at 37° C. for 30 min followed by 7 min at 92° C. This step allows any dephosphorylated oligo 1 to prime a new template strand and at the same time the original template is destroyed by the UNG glycosylase.
8. The contents were then removed from the well and analysed by PCR using 25 pmol primers consisting of oligo 1 and oligo 2 (5' GAG GAT CCC CGG GTA CCG AGC TCG—SEQ ID NO:21) under the following conditions: 93° C. for 30 sec, 65° C. for 30 sec and 72° C. for 10 sec.
9. Aliquots of the PCR were removed at 30 cycles for analysis by electrophoresis on a 30 MetaPhor agarose gel.

Results and Discussion

The combination of ELISA capture and AP modification of a nucleic acid substrate that can be detected by PCR amplification gave a much greater sensitivity for antigen detection than a straightforward ELISA approach.

EXAMPLE 6

Detection of Antigens in an ELISA Format Using an Immobilised Duplex with a 3' Phosphate—the Ligation Approach Introduction This example demonstrates how the invention can be applied in an ELISA format for the detection of antigens such as *Chlamydia* antigens.

Method

1. Maxisorp microtiter plates (Nunc) were coated for 60 min with 100 µl anti-chlamydia LPS antibodies at 0.1-100 ng/ml in TBS (anti-chlamydia antibodies are widely available and are empirically investigated to find a pair that work together in an ELISA format).
2. Wells were washed ×3 with PBS and incubated with 100 µl 1.0-0.01 mg/ml biotinylation reagent (biotin amidocaproic acid 3-sulfo N-hydroxy succinimide ester, Sigma B1022) in PBS for 30 min.
3. Wells were washed ×3 with TBS then incubated with 100 ng/ml streptavidin in TBS 0.5% Tween20 for 60 min. Wells are then washed ×5 with TBS Tween20.
4. Serial dilution of chlamydia LPS antigen were made in TBS 0.5% Tween20 and 100 µl of each dilution added to a coated well.
5. After 60 min the wells were washed ×3 with TBS Tween20 and 1-10 ng of anti-chlamydia LPS AP conjugate (made following standard procedures) added in PBS Tween20, 1 mM sodium vanadate containing oligo ½ at 50 pmoles/ml [duplex oligo ½ with a 3' biotin at one end and a 3' phosphate at the other end was prepared by heating oligo 1 (5' Biotin GCC GAT ATC GGA CAA CGC CGA ACT GCG AAG GGC CAA GGC TCG 3' phosphate—SEQ ID NO:22) with oligo 2 (5' CCT TGG CCC TTC GCA GTT CGG CGT TGT CCG ATA TCG GC 3' Biotin—SEQ ID NO:16) both at 50 pmol/µl in TBS to 90° C. for 5 min followed by slow cooling to room temperature].
6. After 60 min the wells were washed ×5 in TBS tween20 and 50 µl of detection duplex oligo ⅚ added [duplex oligo ⅚ with a complementary 5' phosphate single stranded overhang to the bound oligo duplex ½ was prepared by heating oligo 5 (5' GGT CAT CAG CCG CGT GGC CTT TGT CAC CGA CGC CTA—SEQ ID NO:17) with oligo 6 (5' phosphate TAG GCG TCG GTG ACA AAG GCC ACG CGG CTG ATG ACG—SEQ ID NO:18) both at 50 pmol/µl in TBS to 90° C. for 5 min followed by slow cooling to room temperature] at 1 nmol/ml in 1× ligase buffer containing 400 units/ml T4 DNA ligase (New England Biolabs).
7. After 60 min at room temperature the wells were washed ×4 in TBS 0.5% Tween20 and 50 µl of standard PCR mix added (New England Biolabs) containing Taq DNA polymerase and primers 5' GGA CAA CGC CGA ACT GCG AAG GGC (SEQ ID NO:7) and 5' TAG GCG TCG GTG ACA AAG GCC ACG (SEQ ID NO:8). This was overlayed with 50 µl of mineral oil and heated on a flat heating block at 92° C. for 7 min.
8. The liquid was removed and PCR-performed under the following conditions: 93° C. for 30 sec, 60° C. for 30 sec and 72° C. for 10 sec.
9. Aliquots of the PCR were removed at 30 cycles for analysis by electrophoresis on a 3% MetaPhor agarose gel.

Results and Discussion

The combination of ELISA capture and AP modification of a nucleic acid substrate that can be detected by PCR amplification gave a much greater sensitivity for antigen detection than a straightforward ELISA approach.

EXAMPLE 7

Detection of Antigens in an ELISA Format Using a Non-Immobilised Duplex with a 3' Phosphate—the Ligation Approach Introduction This example demonstrates how the invention can be applied in an ELISA format for the detection of antigens such as *Chlamydia* antigens.

Method

1. Maxisorp microtiter plates (Nunc) were coated for 60 min with 100 µl anti-chlamydia LPS antibodies at 0.1-100 ng/ml in TBS (anti-chlamydia antibodies are widely available and are empirically investigated to find a pair that work together in an ELISA format).
2. Serial dilution of chlamydia LPS antigen were made in TBS 0.5% Tween20 and 100 µl of each dilution added to a coated well. Urinary tract swabs can be extracted using standard techniques into similar-buffer and tested in a similar way.
3. After 60 min the wells were washed ×3 with TBS Tween20 and 0.1-10 ng of anti-chlamydia LPS AP conjugate (made following standard procedures) added in TBS Tween20.
4. After 60 min the wells were washed ×5 in TBS Tween20 and incubated with 100 µl TBS containing oligo ½ at 50 pmoles/ml [duplex oligo ½ with a 3' biotin at one end and a 3' phosphate at the other end was prepared by heating oligo 1 (5' GCC GAT ATC GGA CAA CGC CGA ACT GCG AAG GGC CAA GGC TCG 3' phosphate—SEQ ID NO:15) with oligo 2 (5' CCT TGG CCC TTC GCA GTT CGG CGT TGT CCG ATA TCG GC 3' Biotin—SEQ ID NO:16) both at 50 pmol/µl in TBS to 90° C. for 5 min followed by slow cooling to room temperature].
5. After 10-30 min 10 µl of TBS containing 10 mM ATP, 10 mM MgCl2, 10 units T4 DNA ligase and 0.5-50 pmoles detection duplex oligo ⅚ was added [duplex oligo ⅚ with a complementary 5' phosphate single stranded overhang to the bound oligo duplex ½ was prepared by heating oligo 5 (5' GGT CAT CAG CCG CGT GGC CTT TGT CAC CGA CGC CTA—SEQ ID NO:17) with oligo 6 (5' phosphate TAG GCG TCG GTG ACA AAG GCC ACG CGG CTG ATG ACG—SEQ ID NO:18) both at 50 pmol/µl in TBS to 90° C. for 5 min followed by slow cooling to room temperature].
6. After 60 min at room temperature 5 µl of the reaction was removed for PCR following a standard protocol in a total volume of 50 µl with primers 5' GGA CAA CGC CGA ACT GCG AAG GGC (SEQ ID NO:7) and 5' TAG GCG TCG GTG ACA AAG GCC ACG (SEQ ID NO:8) under the following conditions: 93° C. for 30 sec, 65° C. for 30 sec and 72° C. for 10 sec.

7. Aliquots of the PCR were removed at 30 cycles for analysis by electrophoresis on a 31 MetaPhor agarose gel.

Results and Discussion

The combination of ELISA capture and AP modification of a nucleic acid substrate that can be detected by PCR amplification gave a much greater sensitivity for antigen detection than a straightforward ELISA approach.

EXAMPLE 8

Detection of Antigens in an ELISA Format Using an Non-Immobilised Duplex with a 3' Phosphate—the Extension Approach Introduction This example demonstrates how the invention can be applied in an ELISA format for the detection of antigens such as *Chlamydia* antigens.

Method

1. Maxisorp microtiter plates (Nunc) were coated for 60 min with 100 µl anti-chlamydia LPS antibodies at 0.1-100 ng/ml in TBS (anti-chlamydia antibodies are widely available and are empirically investigated to find a pair that work together in an ELISA format).
2. Serial dilution of chlamydia LPS antigen were made in TBS 0.5% Tween20 and 100 µl of each dilution added to a coated well. Urinary tract swabs can be extracted using standard techniques into similar buffer and tested in a similar way.
3. After 60 min the wells were washed ×3 with TBS Tween20 and 0.1-10 ng of anti-chlamydia LPS AP conjugate (made following standard procedures) added in PBS Tween20.
4. After 60 min the wells were washed ×5 with TBS Tween20 and 100 µl 1×PCR buffer added containing, 10 ng DNA duplex (10 pmoles/ml oligo 1; 5' CCA GGC GAA AGG GGG ATG TGC TGC AA 3' (SEQ ID NO:23) phosphate annealed to long of a denatured template DNA [made by PCR of pUC19 with oligo 1 and oligo 3 (5' TCA CTC GCG TTG CGT TAA TTA CAC TC (SEQ ID NO:20) in a reaction mix in which the normal nucleotide dTTP is replaced by dUTP and then the product purified by affinity chromatography following standard methods], standard quantities of Taq DNA polymerase, 10 units of UNG glycosylase, and standard concentrations of dNTPs.
5. After 10-30 min 50 pmol primers consisting of oligo 1 and oligo 2 (5' GAG GAT CCC CGG GTA CCG AGC TCG—SEQ ID NO:21) were added and the well contents investigated by PCR under the following conditions: 93° C. for 30 sec, 65° C. for 30 sec and 72° C. for 10 sec.
6. Aliquots of the PCR were removed at 30 cycles for analysis by electrophoresis on a 3% MetaPhor agarose gel.

Results and Discussion

The combination of ELISA capture and AP modification of a nucleic acid substrate that can be detected by PCR amplification gave a much greater sensitivity for antigen detection than a straightforward ELISA approach.

EXAMPLE 9

An Embodiment of the Alkaline Phosphatase Assay that Involves the Use of a 3' Phosphate-Blocked DNA Substrate Concept FIG. 7 in particular (but also FIGS. 8 and 9) shows the concept of this approach. The partially double-stranded DNA formed by the annealing of two 3' phosphate blocked oligonucleotides cannot be extended by a polymerase unless the blocking phosphate groups at one or both 3' ends have been removed by phosphatase. Removal of the blocking phosphate group(s) by the phosphatase allows the unblocked strand to be extended by a polymerase (prior to or as part of the PCR process) using the complementary strand as a substrate. This, in turn, creates the complementary binding site for the PCR primer such that the extended DNA is now an appropriate substrate for PCR. The DNA substrate can be incubated in the presence of the phosphatase as a preformed partially double-stranded DNA substrate (as shown below) or as the individual synthetic oligonucleotides that will form the partially double-stranded DNA in the subsequent annealing step of the PCR. It should be noted that in one embodiment, only one synthetic 3' phosphate blocked oligonucleotide need be incubated with the phosphatase. Removal of this phosphate allows the generation of a PCR substrate when this oligonucleotide is subsequently mixed with its partially complementary partner included in the PCR incubation and analysis.

The concept is shown schematically in FIGS. 7 to 9.

This embodiment can be used to detect phosphatase that is immobilized or free in solution. In one example, the method can be used to detect an alkaline phosphatase antibody conjugate that has been immobilized to the surface of a bead or microtiter plate through binding to an immobilized (through antibody capture, for example) antigen. In the example given here, dilutions of alkaline phosphatase are directly immobilized in a microtiter well in order to assess the relative sensitivity of this detection approach compared to standard calorimetric approaches.

Method

Triplicate 10-fold dilutions of calf intestinal alkaline phosphatase in 100 µl TBS and TBS-only controls were immobilized on the surface of micotiter plate wells for 1 hour. After washing in TBS 0.1% (v/v) Tween20 various substrates were added for the detection of the immobilized alkaline phosphatase.

A. One set of dilutions was detected using a sensitive amplified substrate, AMPAQ (Dako Ltd., UK), following the manufacturer's protocol for detection.

B. One set of dilutions was detected following a standard colorimetric pNPP protocol.

C. One set of dilutions was detected using the DNA substrate approach. For this, 100 µl of 50 mM Tris, 10 mM MgCl2, 100 mM NaCl, 1 mM DTT containing 1 pmole each of the synthetic oligonucleotides;

Oligo 121005A, 5' gCC gAT ATC ggA CAA Cgg CCg AAC Tgg gAA ggC gCA Cgg AgA gAC CAC g 3' (SEQ ID NO: 24) phosphate and Oligo 121005B, 5' TAg gCg TCg gTg ACA AAC ggC CAg CTA TgA CTT CgT ggT CTC TCC gTg 3' (SEQ ID NO: 25) phosphate was added and incubated for 60 min at room temperature. After incubation 10 µl of the solution was analysed by standard hot start PCR in a volume of 50 µl. PCR conditions were 1 cycle of 94° C. for 15 min; 5 cycles of 94° C. for 30 sec, 50° C. for 30 sec, 72° C. for 30 sec; 25 cycles of 94° C. for 30 sec, 60° C. for 30 sec, 72° C. for 30 sec; 72° C. for 10 min.

The PCR primers,

```
F, 5' GGACAACGGCCGAACTGGGAAGGCG 3'  (SEQ ID NO: 26)
and
R, 5' TAGGCGTCGGTGACAAACGGCCAGC 3'  (SEQ ID NO: 27)
``` were used in the PCR. After PCR 10 μl of reaction was analysed by agarose gel electrophoresis (see the results, below. In this figure, a negative control containing no phosphatase is included between each phosphatase dilution).

Results

The colorimetric pNpp and AMPAQ substrates detected the $10^{-3}$ and $10^{-6}$ dilutions of alkaline phosphatase, respectively. The 3' phosphate blocked DNA substrate approach was much more sensitive (see FIG. 10) and could detect as low as the $10^{-11}$ dilution of alkaline phosphatase which represents about 600 molecules of alkaline phosphatase.

Discussion

The use of a DNA substrate in combination with an amplification technique such as PCR yields a much more sensitive detection of alkaline phosphatase than standard calorimetric or amplified calorimetric approaches.

The invention claimed is:

1. A method of detecting phosphatase in a sample, which phosphatase is capable of adding or removing terminal phosphates from a nucleic acid molecule, thereby conferring the nucleic acid molecule with the ability to be extended to generate a novel detectable nucleic acid molecule, the method comprising:
   allowing the sample to be tested for the presence of the phosphatase to interact with the nucleic acid molecule; and
   testing for interaction of the phosphatase with the nucleic acid molecule by detecting the novel nucleic acid molecule generated only in the presence of the phosphatase; and
determining the presence of the novel nucleic acid molecule by nucleic acid amplification, thereby detecting the presence of phosphatase in the sample.

2. The method according to claim 1 wherein the terminal phosphates that are removed are present at the 3' end of the nucleic acid molecule.

3. The method according to claim 1 wherein the nucleic acid molecule is a synthesized oligonucleotide which is 3' end labeled with a phosphate group.

4. The method according to claim 1 wherein the phosphatase is alkaline phosphatase or prostatic acid phosphatase.

5. The method according to claim 1 wherein the novel nucleic acid molecule that is detected is generated by ligation of the 3' end of the nucleic acid molecule to the 5' end of a further nucleic acid molecule.

6. The method according to claim 5 wherein the detection step is carried out by incubating the sample with a ligase and the further nucleic acid molecule and testing for the presence of the novel nucleic acid molecule following incubation.

7. The method according to claim 1 wherein the nucleic acid molecule comprises a single stranded DNA molecule in which a terminal 3' phosphate is present and an overlapping single stranded DNA molecule which is blocked at the 3' end such that it cannot be extended.

8. The method according to claim 7 wherein the novel nucleic acid molecule that is detected is generated by polymerization using the nucleic acid molecule originally phosphorylated at the 3'end to prime nucleic acid synthesis, provided the phosphatase is present in the sample to remove the 3' terminal phosphate group, using the overlapping single stranded DNA as a template for synthesis.

9. The method according to claim 1 wherein the nucleic acid molecule comprises partially dsDNA in which terminal 3' phosphates are present.

10. The method according to claim 9 wherein the dsDNA comprises a nick in each strand.

11. The method according to claim 9 wherein the novel nucleic acid molecule that is detected is generated by polymerization using the nucleic acid molecule originally phosphorylated at the 3'end to prime nucleic acid synthesis, provided the phosphatase is present in the sample to remove the 3' terminal phosphate group, using a single stranded element as a template for synthesis.

12. The method according to claim 1 which is used for detection of a phosphatase associated with an infectious agent and comprises specific capture of the phosphatase and whereby detection of the novel nucleic acid molecule indicates the presence of the infectious agent.

13. The method according to claim 12 wherein the specific capture utilizes a specific antibody.

14. The method according to claim 13 wherein the specific antibody is immobilized on a solid support.

15. The method according to claim 12 wherein the infectious agent is *Aspergillus* or *Staphyloccous* species.

* * * * *